United States Patent
Robinson et al.

(10) Patent No.: US 11,324,405 B2
(45) Date of Patent: May 10, 2022

(54) OBSERVATIONAL HEART FAILURE MONITORING SYSTEM

(71) Applicant: Medici Technologies, LLC, Albuquerque, NM (US)

(72) Inventors: Mark Ries Robinson, Albuquerque, NM (US); Elena A Allen, Albuquerque, NM (US)

(73) Assignee: Medici Technologies LLC, Albuquerque, NM (US)

( * ) Notice: Subject to any disclaimer, the term of this patent is extended or adjusted under 35 U.S.C. 154(b) by 449 days.

(21) Appl. No.: 15/780,401

(22) PCT Filed: Dec. 6, 2016

(86) PCT No.: PCT/US2016/065135
§ 371 (c)(1),
(2) Date: May 31, 2018

(87) PCT Pub. No.: WO2017/100185
PCT Pub. Date: Jun. 15, 2017

(65) Prior Publication Data
US 2018/0360325 A1  Dec. 20, 2018

Related U.S. Application Data

(60) Provisional application No. 62/423,701, filed on Nov. 17, 2016, provisional application No. 62/375,431, (Continued)

(51) Int. Cl.
*A61B 5/0205* (2006.01)
*A61B 5/029* (2006.01)
(Continued)

(52) U.S. Cl.
CPC ......... *A61B 5/0205* (2013.01); *A61B 5/0024* (2013.01); *A61B 5/029* (2013.01); (Continued)

(58) Field of Classification Search
CPC ...... A61B 5/029; A61B 5/0208; A61B 5/0205
See application file for complete search history.

(56) References Cited

U.S. PATENT DOCUMENTS

| | | |
|---|---|---|
| 5,291,895 A | 3/1994 | McIntyre |
| 5,649,543 A | 7/1997 | Hosaka |

(Continued)

FOREIGN PATENT DOCUMENTS

| | | |
|---|---|---|
| JP | 2015/519940 | 7/2015 |
| WO | WO2015/049963 | 4/2015 |
| WO | WO2015/092593 | 6/2015 |

OTHER PUBLICATIONS

Van Hoeyweghen, R.; Hanson, J.; Stewart, M. J.; Dethune, L.; Davies, I.; Little, R. A.; Horan, M. A.; Kirkman, E., Cardiovascular Response to Graded Lower Body Negative Pressure in Young and Elderly Man, 2001, Journal : Experimental Physiology.
(Continued)

*Primary Examiner* — Michael J D'Abreu
(74) *Attorney, Agent, or Firm* — V Gerald Grafe

(57) ABSTRACT

Method and systems provide for reliable, convenient, and cost-effective personalized assessment of hemodynamic status in the ambulatory heart failure patient. The method and apparatus use pulse contour analysis of data obtained through observation of the patient for determination of hemodynamic status, and for determination of day-to-day changes in hemodynamic status. Observational assessment of the patient includes monitoring during activities of daily living including sleeping, sitting and standing. These activities create changes in venous return that are used to evaluate cardiac function or changes in cardiac function. The method and system infer body position by using position and motion information obtained by the system. Changes in cardiac function over time or due to changes in body pose are
(Continued)

LVET Changes stability over time evaluated for the assessment of hemodynamic status, with a focus on changes resulting from fluid overload.

22 Claims, 17 Drawing Sheets

Related U.S. Application Data filed on Aug. 15, 2016, provisional application No. 62/263,839, filed on Dec. 7, 2015.

(51) Int. Cl.

| | |
|---|---|
| *A61B 5/021* | (2006.01) |
| *A61B 5/091* | (2006.01) |
| *A61B 5/113* | (2006.01) |
| *A61B 5/024* | (2006.01) |
| *A61B 7/00* | (2006.01) |
| *A61B 5/00* | (2006.01) |
| *A61B 5/349* | (2021.01) |
| *A61B 5/11* | (2006.01) |
| *A61B 5/02* | (2006.01) |

(52) U.S. Cl.
CPC ...... *A61B 5/02125* (2013.01); *A61B 5/02416* (2013.01); *A61B 5/02427* (2013.01); *A61B 5/091* (2013.01); *A61B 5/113* (2013.01); *A61B 5/1126* (2013.01); *A61B 5/349* (2021.01); *A61B 7/00* (2013.01); *A61B 5/02028* (2013.01); *A61B 5/02405* (2013.01); *A61B 5/1116* (2013.01); *A61B 5/1118* (2013.01); *A61B 5/4561* (2013.01); *A61B 5/4812* (2013.01); *A61B 5/6826* (2013.01)

(56) References Cited

U.S. PATENT DOCUMENTS

| | | | |
|---|---|---|---|
| 2003/0036685 A1 | 2/2003 | Goodman | |
| 2005/0143665 A1* | 6/2005 | Huiku | A61B 5/4035 600/500 |
| 2007/0213624 A1 | 9/2007 | Reisfeld | |
| 2008/0200775 A1 | 8/2008 | Lynn | |
| 2009/0030292 A1 | 1/2009 | Bartnik | |
| 2010/0298650 A1 | 11/2010 | Moon | |
| 2014/0247334 A1 | 9/2014 | Johnson et al. | |
| 2015/0351675 A1* | 12/2015 | Cheng | A61B 5/14552 600/323 |
| 2016/0270708 A1 | 9/2016 | Tateda et al. | |
| 2017/0079533 A1* | 3/2017 | Robinson | A61B 5/0075 |
| 2017/0209055 A1* | 7/2017 | Pantelopoulos | A61B 5/02108 |

OTHER PUBLICATIONS

Hassan, S.; Turner, P., Systolic time intervals: a review of the method in the non-invasive investigation of cardiac function in health, disease and clinical pharmacology., 1983, Journal : Postgraduate Medical Journal.

Harms, Mark P M; Wesseling, Karel H; Pott, Frank; Jenstrup, Morten; Goudoever, Jeroen Van; Secher, Niels H; Lieshout, Johannes J Van, Continuous stroke volume monitoring by modelling flow from non-invasive measurement of arterial pressure in humans under orthostatic stress, 1999, Journal : The Biochemical Society and the Medical Research Society.

Harley, Alexander; Starmer, C. Frank; Greenfield, Joseph C., Pressure-flow studies in man. An evaluation of the duration of the phases of systole, 1969, Journal : Journal of Clinical Investigation.

Günther, Sven; Sztrymf, Benjamin; Savale, Laurent; Lau, Edmund M.; Montani, David; Hervé, Philippe; Lador, Frédéric; Jaïs, Xavier; Parent, Florence; Simonneau, Gérald; Sitbon, Olivier; Humbert, Marc; Chemla, Denis, Relation between left ventricular ejection time and pulmonary hemodynamics in pulmonary hypertension, 2015, Journal : International Journal of Cardiology.

Grum, D. F.; Dauchot, P. J. Correlation of Systolic Time Intervals with Stroke Volume in Man, 1980, Book Section: Springer Berlin Heidelberg.

Gheorghiade, Mihai; Filippatos, Gerasimos; De Luca, Leonardo; Burnett, John, Congestion in Acute Heart Failure Syndromes: An Essential Target of Evaluation and Treatment, 2006, Journal : The American Journal of Medicine.

Garrard, Clifford L.; Weissler, Arnold M.; Dodge, Harold T., The Relationship of Alterations in Systolic Time Intervals to Ejection Fraction in Patients with Cardiac Disease, 1970, Journal : Circulation.

Bronzwaer, Anne-Sophie G.T.; Bogert, Lysander W.J.; Westerhof, Berend E.; Piek, Jan J.; Daemen, Mat J.A.P.; van Lieshout, Johannes J., Abnormal haemodynamic postural response in patients with chronic heart failure: Abnormal haemodynamic postural response in patients with chronic heart failure, 2017, Journal : ESC Heart Failure.

Braunschweig, F, Continuous haemodynamic monitoring during withdrawal of diuretics in patients with congestive heart failure, 2002, Journal : European Heart Journal.

Chan, Gregory S H; Middleton, Paul M; Celler, Branko G; Wang, Lu; Lovell, Nigel H, Automatic detection of left ventricular ejection time from a finger photoplethysmographic pulse oximetry waveform: comparison with Doppler aortic measurement, 2007, Journal : Physiological Measurement.

Abraham, William T; Adamson, Philip B; Bourge, Robert C; Aaron, Mark F; Costanzo, Maria Rosa; Stevenson, Lynne W; Strickland, Warren; Neelagaru, Suresh; Ravel, Nirav; Krueger, Steven; Weiner, Stanislav; Shavelle, David; Jeffries, Bradley; Yadav, Jay S, Wireless pulmonary artery haemodynamic monitoring in chronic heart failure: a randomised controlled trial, 2011, Journal : The Lancet.

Abelmann, Walter H.; Fareeduddin, Khaja Increased tolerance of orthostatic stress in patients with heart disease, 1969, Journal : The American Journal of Cardiology.

Sanche, Zambrano, Sergio; Spodick, David H., Comparative Responses to Orthostatic Stress in Normal and Abnormal Subjects, 1974, Journal : Chest.

Wroblewski, H; Kastrup, J; Mortensen, S A; Haunsø, S, Abnormal baroreceptor-mediated vasodilation of the peripheral circulation in congestive heart failure secondary to idiopathic dilated cardiomyopathy., 1993, Journal : Circulation.

Lewis, R P; Rittogers, S E; Froester, W F; Boudoulas, H, A critical review of the systolic time intervals., 1977, Journal : Circulation.

Weissler, Arnold M.; Harris, Willard S.; Schoenfeld, Clyde D., Systolic Time Intervals in Heart Failure in Man, 1968, Journal : Circulation.

Cziesler, Cody R, Using Least Variance for Robust Extraction of Systolic Time Intervals, 2014, Thesis: Rochester Institute of Technology.

Tavel, Morton E.; Baugh, David O.; Feigenbaum, Harvey; Nasser, William K.; Stewart, Janie, Left Ventricular Ejection Time in Atrial Fibrillation, 1972, Journal : Circulation.

Stafford, R. W.; Harris, W. S.; Weissler, A. M., Left Ventricular Systolic Time Intervals as Indices of Postural Circulatory Stress in Man, 1970, Journal : Circulation.

Quarry-Pigott, Veronica; Chirife, Raul; Spodick, David H., Ejection Time by Ear Densitogram and Its Derivative: Clinical and Physiologic Applications, 1973, Journal : Circulation.

Boehmer, John P.; Hariharan, Ramesh; Devecchi, Fausto G.; Smith, Andrew L.; Molon, Giulio; Capucci, Alessandro; An, Qi; Averina, Viktoria; Stolen, Craig M.; Thakur, Pramodsingh H.; Thompson, Julie A.; Wariar, Ramesh; Zhang, Yi; Singh, Jagmeet P., A Multisensor Algorithm Predicts Heart Failure Events in Patients With Implanted Devices, 2017, Journal : JACC: Heart Failure.

Jansen, J.R.C.; Schreuder, J.J.; Mulier, J.P.; Smith, N.T.; Settels, J.J.; Wesseling, K.H., A comparison of cardiac output derived from the arterial pressure wave against thermodilution in cardiac surgery patients †, 2001, Journal : British Journal of Anaesthesia.

Abay, T. Y.; Kyriacou, P. A., Accuracy of reflectance photoplethysmography on detecting cuff-induced vascular occlusions, 2015, Conference: IEEE.

(56) References Cited

OTHER PUBLICATIONS

Addison, Paul S.; Wang, Rui; Uribe, Alberto A.; Bergese, Sergio D., Increasing signal processing sophistication in the calculation of the respiratory modulation of the photoplethysmogram (DPOP), 2015, Journal : Journal of Clinical Monitoring and Computing.

Ng, Jason; Sahakian, Alan V; Swiryn, Steven, Accelerometer-Based Body-Position Sensing for Ambulatory Electrocardiographic Monitoring, 2003, Journal : Biomedical Instrumentation.

Alastruey, Jordi; Passerini, Tiziano; Formaggia, Luca; Peiró, Joaquim, Physical determining factors of the arterial pulse waveform: theoretical analysis and calculation using the 1-D formulation, 2012, Journal : Journal of Engineering Mathematics.

Alastruey, Jordi; Parker, Kim H; Sherwin, Spencer J, Arterial pulse wave haemodynamics, 2012, 11th International Conference on Pressure Surges; 2012. pp. 401-443.

Allen, J; Murray, A, Age-related changes in peripheral pulse timing characteristics at the ears, fingers and toes, 2002, Journal : Journal of Human Hypertension.

He, David Da; Winokur, Eric S.; Sodini, Charles G., An Ear-Worn Vital Signs Monitor, 2015, Journal : IEEE Transactions on Biomedical Engineering.

Gheorghiade, Mihai; Follath, Ferenc; Ponikowski, Piotr; Barsuk, Jeffrey H.; Blair, John E.A.; Cleland, John G.; Dickstein, Kenneth; Drazner, Mark H.; Fonarow, Gregg C.; Jaarsma, Tiny; Jondeau, Guillaume; Sendon, Jose Lopez; Mebazaa, Alexander; Metra, Marco; Nieminen, Markku; Pang, Peter S.; Seferovic, Petar; Stevenson, Lynne W.; van Veldhuisen, Dirk J.; Zannad, Faiez; Anker, Stefan D.; Rhodes, Andrew; McMurray, John J.V.; Filippatos, Gerasimos, Assessing and grading congestion in acute heart failure: a scientific statement from the Acute Heart Failure Committee of the Heart Failure Association of the European Society of Cardiology and endorsed by the European Society of Intensive Care Medicine, 2010, Journal : European Journal of Heart Failure.

Couceiro, Ricardo; Carvalho, P; Paiva, R P; Henriques, J; Quintal, I; Antunes, M; Muehlsteff, J; Eickholt, C; Brinkmeyer, C; Kelm, M; Meyer, C, Assessment of cardiovascular function from multi-Gaussian fitting of a finger photoplethysmogram, 2015, Journal : Physiological Measurement.

Awad, Aymen A.; Stout, Robert G.; Ghobashy, M. Ashraf M.; Rezkanna, Hoda A.; Silverman, David G.; Shelley, Kirk H., Analysis of the Ear Pulse Oximeter Waveform, 2006, Journal : Journal of Clinical Monitoring and Computing.

Barnas, Michel G W; Boer, Walther H; Koomans, Hein A, Hemodynamic Patterns and Spectral Analysis of Heart Rate Variability during Dialysis Hypotension, 1999, Journal : J Am Soc Nephrol.

Baruch, Martin C; Warburton, Darren ER; Bredin, Shannon SD; Cote, Anita; Gerdt, David W; Adkins, Charles M, Pulse Decomposition Analysis of the digital arterial pulse during hemorrhage simulation, 2011, Journal : Nonlinear Biomedical Physics.

Bendjelid, Karim, The pulse oximetry plethysmographic curve revisited:, 2008, Journal : Current Opinion in Critical Care.

Bogert, Lysander W. J.; van Lieshout, Johannes J., Non-invasive pulsatile arterial pressure and stroke volume changes from the human finger: noninvasive pressure and flow, 2005, Journal : Experimental Physiology.

Bonomi, Alberto G.; Goris, Annelies H.C.; Yin, Bin; Westerterp, Klaas R., Detection of Type, Duration, and Intensity of Physical Activity Using an Accelerometer:, 2009, Journal : Medicine & Science in Sports & Exercise.

Smith, D; Craige, E, Mechanism of the dicrotic pulse., 1986, Journal : Heart.

Broccard, Alain F., Cardiopulmonary interactions and volume status assessment, 2012, Journal : Journal of Clinical Monitoring and Computing.

Bronzwaer, Anne-Sophie G. T.; Ouweneel, Dagmar M.; Stok, Wim J.; Westerhof, Berend E.; van Lieshout, Johannes J., Arterial Pressure Variation as a Biomarker of Preload Dependency in Spontaneously Breathing Subjects—A Proof of Principle, 2015, Journal : PLOS One.

Nieminen, T.; Koobi, T.; Turjanmaa, V., Can stroke volume and cardiac output be determined reliably in a tilt-table test using the pulse contour method?, 2000, Journal : Clinical Physiology.

Miller, J C; Horvath, S M, Cardiac Output During Human Sleep, 1976, Journal : avation, space and environmental medicine.

De Wilde, R. B. P.; Schreuder, J. J.; van den Berg, P. C. M.; Jansen, J. R. C., An evaluation of cardiac output by five arterial pulse contour techniques during cardiac surgery, 2007, Journal Anaesthesia.

Costanzo, Maria R.; Stevenson, Lynne W.; Adamson, Philip B.; Desai, Akshay S.; Heywood, J. Thomas; Bourge, Robert C.; Bauman, Jordan; Abraham, William T., Interventions Linked to Decreased Heart Failure Hospitalizations During Ambulatory Pulmonary Artery Pressure Monitoring, 2016, Journal : JACC: Heart Failure.

Cavallaro, Fabio; Sandroni, Claudio; Marano, Cristina; La Torre, Giuseppe; Mannocci, Alice; De Waure, Chiara; Bello, Giuseppe; Maviglia, Riccardo; Antonelli, Massimo, Diagnostic accuracy of passive leg raising for prediction of fluid responsiveness in adults: systematic review and meta-analysis of clinical studies, 2010, Journal : Intensive Care Medicine.

Chan, Gregory S. H.; Middleton, Paul M.; Celler, Branko G.; Wang, Lu; Lovell, Nigel H., Change in pulse transit time and pre-ejection period during head-up tilt-induced progressive central hypovolaemia, 2007, Journal : Journal of Clinical Monitoring and Computing.

Middleton, Paul M.; Chan, Gregory S.H.; O'Lone, Emma; Steel, Elizabeth; Carroll, Rebecca; Celler, Branko G.; Lovell, Nigel H., Changes in left ventricular ejection time and pulse transit time derived from finger photoplethysmogram and electrocardiogram during moderate haemorrhage, 2009, Journal : Clinical Physiology and Functional Imaging.

Chen, Yuqing; Xue, Yang, A Deep Learning Approach to Human Activity Recognition Based on Single Accelerometer, 2015, Conference: IEEE.

Chernbumroong, S.; Atkins, A. S.; Hongnian Yu, Activity classification using a single wrist-worn accelerometer, 2011, Conference: IEEE.

Martin, C. Edwin; Shaver, James A.; Thompson, Mark E.; Reddy, P. Sudhakar; Leonard, James J., Direct Correlation of External Systolic Time Intervals with Internal Indices of Left Ventricular Function in Man, 1971, Journal : Circulation.

Su, Ho-Ming; Lin, Tsung-Hsien; Hsu, Po-Chao; Chu, Chun-Yuan; Lee, Wen-Hsien; Chen, Szu-Chia; Lee, Chee-Siong; Voon, Wen-Chol; Lai, Wen-Ter; Sheu, Sheng-Hsiung, A Comparison between Brachial and Echocardiographic Systolic Time Intervals, 2013, Journal : PLoS One.

Convertino, Victor A.; Ratliff, Duane A.; Ryan, Kathy L.; Doerr, Donald F.; Ludwig, David A.; Muniz, Gary W.; Britton, Deanna L.; Clah, Savran D.; Fernald, Kathleen B.; Ruiz, Alicia F.; Lurie, Keith G.; Idris, Ahamed H., Hemodynamics associated with breathing through an inspiratory impedance threshold device in human volunteers:, 2004, Journal : Critical Care Medicine.

Convertino, Victor A.; Moulton, Steven L.; Grudic, Gregory Z.; Rickards, Caroline A.; Hinojosa-Laborde, Carmen; Gerhardt, Robert T.; Blackbourne, Lorne H.; Ryan, Kathy L., Use of Advanced Machine-Learning Techniques for Noninvasive Monitoring of Hemorrhage:, 2011, Journal : The Journal of Trauma: Injury, Infection, and Critical Care.

Hoeksel, S. A. A. P., et al; J.A. Blom, PhD,3 and J.J. Schreuder,MD, PhD1, Detection of Dicrotic Notch in Arterial Pressure Signals, 1997, Journal : Journal of Clinical Monitoring.

Duarte-Dyck, D.; Guillén-Peralta, A.; Romo-Cárdenas, G.; Callorda-Fedeczko, L., Development of an Anatomical Measurement and Data Analysis Tool Based on the Kinect Sensor for Physical Rehabilitation Applications., 2015, Book Section: Springer International Publishing.

Dong, Zhou-zhou, Passive leg raising as an indicator of fluid responsiveness in patients with severe sepsis, 2012, Journal : World Journal of Emergency Medicine.

Carvalho, P; Paiva, R P; Couceiro, R; Henriques, J; Antunes, M; Quintal, I; Muehlsteff, J; Aubert, X, Comparison of systolic time interval measurement modalities for portable devices, 2010, Conference: IEEE.

(56) References Cited

OTHER PUBLICATIONS

Jellema, Wilbert T.; Imholz, Ben P. M.; Oosting, Hans; Wesseling, Karel H.; van Lieshout, Johannes J., Estimation of beat-to-beat changes in stroke volume from arterial pressure: A comparison of two pressure wave analysis techniques during head-up tilt testing in young, healthy men, 1999, Journal : Clinical Autonomic Research.
Javed, Faizan; Middleton, Paul M; Malouf, Philip; Chan, Gregory S H; Savkin, Andrey V; Lovell, Nigel H; Steel, Elizabeth; Mackie, James, Frequency spectrum analysis of finger photoplethysmographic waveform variability during haemodialysis, 2010, Journal : Physiological Measurement.
Heenen, Sarah; Backer, Daniel De; Vincent, Jean-Louis, How can the response to volume expansion in patients with spontaneous respiratory movements be predicted?, 2006, Journal : Critical Care.
Préau, Sébastien; Dewavrin, Florent; Soland, Vincent; Bortolotti, Perrine; Colling, Delphine; Chagnon, Jean-luc; Durocher, Alain; Saulnier, Fabienne, Hemodynamic Changes during a Deep Inspiration Maneuver Predict Fluid Responsiveness in Spontaneously Breathing Patients, 2012, Journal : Cardiology Research and Practice.
Hickey, Michelle; Phillips, Justin P.; Kyriacou, Panayiotis, Venous pooling and drainage affects photoplethysmographic signals at different vertical hand positions, 2015, Conference: SPIE BiOS.
Bui, Anh L.; Fonarow, Gregg C., Home Monitoring for Heart Failure Management, 2012, Journal : Journal of the American College of Cardiology.
Cokkinos, D V; Heimonas, E T; Demopoulos, J N; Harralambakis, A; Tsartsalis, G; Gardikas, C D Influence of heart rate increase on uncorrected pre-ejection period/left ventricular ejection time (PEP/LVET) ratio in normal individuals., 1976, Journal : Heart.
Mertens, H. M.; Mannebach, H.; Trieb, G.; Gleichmann, U., Influence of heart rate on systolic time intervals: Effects of atrial pacing versus dynamic exercise, 1981, Journal : Clinical Cardiology.
Kuntamalla, Srinivas; Ram Gopal Reddy, L., An Efficient and Automatic Systolic Peak Detection Algorithm for Photoplethysmographic Signals, 2014, Journal : International Journal of Computer.
Lansdorp, B.; Lemson, J.; van Putten, M.J.A.M.; de Keijzer, A.; van der Hoeven, J.G.; Pickkers, P., Dynamic indices do not predict volume responsiveness in routine clinical practice, 2012, Journal : British Journal of Anaesthesia.
Lee, Qim Y; Redmond, Stephen J; Chan, Gregory SH; Middleton, Paul M; Steel, Elizabeth; Malouf, Philip; Critoph, Cristopher; Flynn, Gordon; O'Lone, Emma; Lovell, Nigel H, Estimation of cardiac output and systemic vascular resistance using a multivariate regression model with features selected from the finger photoplethysmogram and routine cardiovascular measurements, 2013, Journal : BioMedical Engineering OnLine.
Levick, J. R., An introduction to cardiovascular physiology, 1991, Book: Butterworths.
Levine, B D; Lane, L D; Buckey, J C; Friedman, D B; Blomqvist, C G, Left ventricular pressure-volume and Frank-Starling relations in endurance athletes. Implications for orthostatic tolerance and exercise performance., 1991, Journal : Circulation.
Yinbo Liu; Poon, C.C.Y.; Yuan-Ting Zhang; Yip, G.W.K.; Cheuk-Man Yu, A novel method for assessing arterial stiffness by a hydrostatic approach, 2009, Conference: IEEE.
Maizel, Julien; Airapetian, Norair; Lorne, Emmanuel; Tribouilloy, Christophe; Massy, Ziad; Slama, Michel, Diagnosis of central hypovolemia by using passive leg raising, 2007, Journal : Intensive Care Medicine.
Marik, Paul E., Techniques for Assessment of Intravascular Volume in Critically Ill Patients, 2009, Journal : Journal of Intensive Care Medicine.
Marik, Paul E; Monnet, Xavier; Teboul, Jean-Louis, Hemodynamic parameters to guide fluid therapy, 2011, Journal : Annals of Intensive Care.
Quwaider, Muhannad; Biswas, Subir, Body Posture Identification using Hidden Markov Model with a Wearable Sensor Network, 2008, Conference: ICST.
Mathie, M. J.; Celler, B. G.; Lovell, N. H.; Coster, A. C. F., Classification of basic daily movements using a triaxial accelerometer, 2004, Journal : Medical & Biological Engineering & Computing.
McGrath, Susan P.; Ryan, Kathy L.; Wendelken, Suzanne M.; Rickards, Caroline A.; Convertino, Victor A., Pulse Oximeter Plethysmographic Waveform Changes in Awake, Spontaneously Breathing, Hypovolemic Volunteers:, 2011, Journal : Anesthesia & Analgesia.
Middleton, Paul M.; Chan, Gregory S. H.; O'Lone, Emma; Steel, Elizabeth; Carroll, Rebecca; Celler, Branko G.; Lovell, Nigel H., Spectral Analysis of Finger Photoplethysmographic Waveform Variability in a Model of Mild to Moderate Haemorrhage, 2008, Journal : Journal of Clinical Monitoring and Computing.
Millasseau, Sandrine C; Ritter, James M; Takazawa, Kenji; Chowienczyk, Philip J, Contour analysis of the photoplethysmographic pulse measured at the finger:, 2006, Journal :Journal of Hypertension.
Monnet, Xavier; Rienzo, Mario; Osman, David; Anguel, Nadia; Richard, Christian; Pinsky, Michael R.; Teboul, Jean-Louis, Passive leg raising predicts fluid responsiveness in the critically ill:, 2006, Journal : Critical Care Medicine.
Najafi, B.; Aminian, K.; Loew, F.; Blanc, Y.; Robert, P.A., Measurement of stand-sit and sit-stand transitions using a miniature gyroscope and its application in fall risk evaluation in the elderly, 2002, Journal : IEEE Transactions on Biomedical Engineering.
Najafi, B.; Aminian, K.; Paraschiv-Ionescu, A.; Loew, F.; Bula, C.J.; Robert, P., Ambulatory system for human motion analysis using a kinematic sensor: monitoring of daily physical activity in the elderly, 2003, Journal : IEEE Transactions on Biomedical Engineering.
Natalini, Giuseppe; Rosano, Antonio; Taranto, Maria; Faggian, Barbara; Vittorielli, Elena; Bernardini, Achille, Arterial Versus Plethysmographic Dynamic Indices to Test Responsiveness for Testing Fluid Administration in Hypotensive Patients: A Clinical Trial:, 2006, Journal : Anesthesia & Analgesia.
Zaidi, S N; Collins, S M, Orthostatic stress and area under the curve of photoplethysmography waveform, 2016, Journal : Biomedical Physics & Engineering Express.
Meredith, D. J.; Clifton, D.; Charlton, P.; Brooks, J.; Pugh, C. W.; Tarassenko, L., Photoplethysmographic derivation of respiratory rate: a review of relevant physiology, 2012, Journal : Journal of Medical Engineering & Technology.
Pizov, Reuven; Tamir, Ada; Gelman, Simon, Arterial and Plethysmographic Waveform Analysis in Anesthetized Patients with Hypovolemia, 2010, Journal : Anesthesiology.
Pizov, R.; Eden, A.; Bystritski, D.; Kalina, E.; Tamir, A.; Gelman, S., Hypotension during gradual blood loss: waveform variables response and absence of tachycardia, 2012, Journal : British Journal of Anaesthesia.
Reddy, K.A.; George, B.; Kumar, V.J., Use of Fourier Series Analysis for Motion Artifact Reduction and Data Compression of Photoplethysmographic Signals, 2009, Journal : IEEE Transactions on Instrumentation and Measurement.
Feissel, Marc; Teboul, Jean-Louis; Merlani, Paolo; Badie, Julio; Faller, Jean-Pierre; Bendjelid, Karim, Plethysmographic dynamic indices predict fluid responsiveness in septic ventilated patients, 2007, Journal : Intensive Care Medicine.
Raamat, Rein; Jagomägi, Kersti; Talts, Jaak, Calibrated photoplethysmographic estimation of digital pulse volume and arterial compliance, 2007, Journal : Clinical Physiology and Functional Imaging.
Rickards, Caroline A.; Vyas, Nisarg; Ryan, Kathy L.; Ward, Kevin R.; Andre, David; Hurst, Gennifer M.; Barrera, Chelsea R.; Convertino, Victor A., Are you bleeding? Validation of a machine-learning algorithm for determination of blood volume status: application to remote triage, 2014, Journal : Journal of Applied Physiology.
Rosenkranz, S.; Mayer, C.; Kropf, J.; Wassertheurer, S., Intelligent multichannel sensors for pulse wave analysis, 2011, Journal : Mathematics and Computers in Simulation.
Rowlands, Alex V.; Olds, Tim S.; Hillsdon, Melvyn; Pulsford, Richard; Hurst, Tina L.; Eston, Roger G.; Gomersall, Sjaan R.; Johnston, Kylie; Langford, Joss, Assessing Sedentary Behavior with

(56) References Cited

OTHER PUBLICATIONS the GENEActiv: Introducing the Sedentary Sphere, 2014, Journal : Medicine & Science in Sports & Exercise.

Rubins, Uldis, Finger and ear photoplethysmogram waveform analysis by fitting with Gaussians, 2008, Journal : Medical & Biological Engineering & Computing.

Selvaraj, Nandakumar; Shelley, Kirk H.; Silverman, David G.; Stachenfeld, Nina; Galante, Nicholas; Florian, John P.; Mendelson, Yitzhak; Chon, Ki H., A Novel Approach Using Time—Frequency Analysis of Pulse-Oximeter Data to Detect Progressive Hypovolemia in Spontaneously Breathing Healthy Subjects, 2011, Journal : IEEE Transactions on Biomedical Engineering.

Smorenberg, Annemieke; Lust, Erik J.; Beishuizen, Albertus; Meijer, Jan H.; Verdaasdonk, Ruud M.; Groeneveld, A.B. Johan, Systolic time intervals vs invasive predictors of fluid responsiveness after coronary artery bypass surgery†, 2013, Journal : European Journal of Cardio-Thoracic Surgery.

Tahvanainen, Anna; Leskinen, Miia; Koskela, Jenni; Ilveskoski, Erkki; Nordhausen, Klaus; Oja, Hannu; Kähönen, Mika; Kööbi, Tiit; Mustonen, Jukka; Pörsti, Ilkka, Ageing and cardiovascular responses to head-up tilt in healthy subjects, 2009, Journal : Atherosclerosis.

Klersy, Catherine; De Silvestri, Annalisa; Gabutti, Gabriella; Regoli, François; Auricchio, Angelo, A Meta-Analysis of Remote Monitoring of Heart Failure Patients, 2009, Journal : Journal of the American College of Cardiology.

Wilkins, Robert W.; Halperin, Meyer H.; Litter, Julius, The Effect of the Dependent Position upon Blood Flow in the Limbs, 1950, Journal : Circulation.

Hickey, M; Phillips, J P; Kyriacou, P A, The effect of vascular changes on the photoplethysmographic signal at different hand elevations, 2015, Journal : Physiological Measurement.

Pan, Rémy C Martin-Du; Benoit, Raymond; Girardier, Lucia, The role of body position and gravity in the symptoms and treatment of various medical diseases, 2004, Journal : Swiss Med Wkly.

Suehiro, Koichi; Okutani, Ryu, Influence of tidal volume for stroke volume variation to predict fluid responsiveness in patients undergoing one-lung ventilation, 2011, Journal : Journal of Anesthesia.

Grubb, Blair P.; Kosinski, Daniel, Tilt Table Testing: Concepts and Limitations, 1997, Journal : Pacing and Clinical Electrophysiology.

Klein, Liviu, Treating Hemodynamic Congestion Is the Key to Prevent Heart Failure Hospitalizations, 2016, Journal : JACC: Heart Failure.

Troiano, Richard P; McClain, James J; Brychta, Robert J; Chen, Kong Y, Evolution of accelerometer methods for physical activity research, 2014, Journal : British Journal of Sports Medicine.

Uretzky, G; Palti, Y, A method for comparing transmitted and reflected light photoelectric plethysmography., 1971, Journal : Journal of Applied Physiology.

Jayasree, V K, Selected Cardiovascular Studies Based on Photoplethysmography Technique, 2009, Thesis: Cochin University of Science and Technology.

Raj, Satish R.; Robertson, David; , Biaggioni, Italo; Diedrich, André Abnormal Valsalva Maneuver Is Not Always a Sign of Congestive Heart Failure, 2007, Journal : The American Journal of Medicine.

Van Hees, Vincent T.; Fang, Zhou; Langford, Joss; Assah, Felix; Mohammad, Anwar; da Silva, Inacio C. M.; Trenell, Michael I.; White, Tom; Wareham, Nicholas J.; Brage, Søren, Autocalibration of accelerometer data for free-living physical activity assessment using local gravity and temperature: an evaluation on four continents, 2014, Journal : Journal of Applied Physiology.

Wang, Chien-Hao; Lu, Cheng- Wei; Lin, Tzu-Yu; Abbod, Maysam F; Shieh, Jiann-Shing, An Assessment of Pulse Transit Time for Detecting Heavy Blood Loss During Surgical Operation, 2012, Journal : The Open Biomedical Engineering Journal.

Wang, Lu; Xu, Lisheng; Feng, Shuting; Meng, Max Q.-H.; Wang, Kuanquan, Multi-Gaussian fitting for pulse waveform using Weighted Least Squares and multi-criteria decision making method, 2013, Journal : Computers in Biology and Medicine.

Antonelli, L.; Ohley, W.; Khamlach, R., Dicrotic notch detection using wavelet transform analysis, 1994, Conference: IEEE.

Di Rienzo, M.; Meriggi, P.; Vaini, E.; Castiglioni, P.; Rizzo, F., 24h seismocardiogram monitoring in ambulant subjects, 2012, Conference: IEEE.

Weissler, Arnold M.; Peeler, Robert G.; Roehll, Walter H., Relationships between left ventricular ejection time, stroke volume, and heart rate in normal individuals and patients with cardiovascular disease, 1961, Journal : American Heart Journal.

Zöllei, Éva; Bertalan, Viktória; Németh, Andrea; Csábi, Péter; László, Ildikó; Kaszaki, József; Rudas, László, Non-invasive detection of hypovolemia or fluid responsiveness in spontaneously breathing subjects, 2013, Journal : BMC Anesthesiology.

Paiva, R.P.; Carvalho, P.; Aubert, X.; Muehlsteff, J.; Henriques, J.; Antunes, M., Assessing PEP and LVET from heart sounds: Algorithms and evaluation, 2009, Conference: IEEE.

Akhtar, Shamsuddin; Matei, Veronica; London, Martin J.; Barash, Paul G., Electrocardiographic Monitoring, 2011, Book Section: Elsevier BV.

Teboul, J. -L.; Lamia, B.; Monnet, X., Assessment of Fluid Responsiveness in Spontaneously Breathing Patients, 2007, Conference: Springer Berlin Heidelberg.

Monge García, Manuel Ignacio; Gil Cano, Anselmo; Díaz Monrové, Juan Carlos, Arterial pressure changes during the Valsalva maneuver to predict fluid responsiveness in spontaneously breathing patients, 2008, Journal : Intensive Care Medicine.

Amoroso, P.; Greenwood, R. N., Posture and central venous pressure measurement in circulatory volume depletion, 1989, Journal : Lancet.

Hickey, Michelle; Phillips, Justin P.; Kyriacou, Panayiotis A., Investigation of peripheral photoplethysmographic morphology changes induced during a hand-elevation study, 2016, Journal : Journal of Clinical Monitoring and Computing.

Weissler, Arnold M.; Harris, Leonard C.; White, George D., Left ventricular ejection time index in man, 1963, Journal : Journal of Applied Physiology.

Murata, K.; Yamane, O.; Suga, H.; Yamamoto, S.; Kogure, S.; Hojo, Y.; Baba, N., Alterations of circulatory responses to upright tilt in cardiac patients, 1981, Journal : Japanese Heart Journal.

Ong, Michael K.; Romano, Patrick S.; Edgington, Sarah; Aronow, Harriet U.; Auerbach, Andrew D.; Black, Jeanne T.; De Marco, Teresa; Escarce, Jose J.; Evangelista, Lorraine S.; Hanna, Barbara; Ganiats, Theodore G.; Greenberg, Barry H.; Greenfield, Sheldon; Kaplan, Sherrie H.; Kimchi, Asher; Liu, Honghu; Lombardo, Dawn; Mangione, Carol M.; Sadeghi, Bahman; Sadeghi, Banafsheh; Sarrafzadeh, Majid; Tong, Kathleen; Fonarow, Gregg C.; for the Better Effectiveness After Transition—Heart Failure (BEAT-HF) Research Group, Effectiveness of Remote Patient Monitoring After Discharge of Hospitalized Patients With Heart Failure: The Better Effectiveness After Transition—Heart Failure (BEAT-HF) Randomized Clinical Trial, 2016, Journal : JAMA Internal Medicine.

Stevenson, Lynne Warner; Perloff, Joseph K., The Limited Reliability of Physical Signs for Estimating Hemodynamics in Chronic Heart Failure, 1989, Journal : JAMA.

Lewin, Jennifer; Ledwidge, Mark; O'Loughlin, Christina; McNally, Clare; McDonald, Ken, Clinical deterioration in established heart failure: What is the value of BNP and weight gain in aiding diagnosis?, 2005, Journal : European Journal of Heart Failure.

Tamura, Toshiyo; Maeda, Yuka; Sekine, Masaki; Yoshida, Masaki, Wearable Photoplethysmographic Sensors—Past and Present, 2014, Journal : Electronics.

Jihyoung Lee; Matsumura, Kenta; Yamakoshi, Ken-ichi; Rolfe, Peter; Tanaka, Shinobu; Yamakoshi, Takehiro, Comparison between red, green and blue light reflection photoplethysmography for heart rate monitoring during motion, 2013, Conference: IEEE.

Sokwoo Rhee; Boo-Ho Yang; Asada, H.H. Artifact-resistant power-efficient design of finger-ring plethysmographic sensors, 2001, Journal : IEEE Transactions on Biomedical Engineering.

Sola, J.; Castoldi, S.; Chetelat, O.; Correvon, M.; Dasen, S.; Droz, S.; Jacob, N.; Kormann, R.; Neumann, V.; Perrenoud, A.; Pilloud, P.; Verjus, C.; Viardot, G., SpO2 Sensor Embedded in a Finger Ring: design and implementation, 2006, Conference: IEEE.

(56) References Cited

OTHER PUBLICATIONS

Sola, Josep; Chetelat, Olivier, Combination of multiple light paths in pulse oximetry: the finger ring example, 2007, Conference: IEEE.

Maeda, Yuka; Sekine, Masaki; Tamura, Toshiyo, Relationship Between Measurement Site and Motion Artifacts in Wearable Reflected Photoplethysmography, 2011, Journal : Journal of Medical Systems.

Maeda, Yuka; Sekine, Masaki; Tamura, Toshiyo, The Advantages of Wearable Green Reflected Photoplethysmography, 2011, Journal : Journal of Medical Systems.

De Paula, Erich Vinicius, Tides within ourselves: how posture can affect blood volume, blood cells and clinical reasoning, 2017, Journal : Revista Brasileira de Hematologia e Hemoterapia.

O'Rourke, Michael F; Gallagher, David E, Pulse wave analysis. 1996, Journal : Journal of hypertension. Supplement: official journal of the International Society of Hypertension.

Fan, Zhaopeng; Zhang, Gong; Lia, Simon, Pulse Wave Analysis, 2011, Book Section: IntechOpen.

Weissler, Arnold M., Systolic-time intervals, 1977, Journal : New England Journal of Medicine.

Levick, J. Rodney, An introduction to cardiovascular physiology, 2013, Book Section: Butterworth-Heinemann.

Sami, A., et al., Passive leg rising and pulse contour monitoring, 2006, Journal: Critical Care; p. 338 (2006).

Weissler, Arnold M., Leonard C. Harris, and George D. White, Left Ventricular Ejection Time in man, 1963, Journal : Journal of applied physiology.

Cherpanath, Thomas GV, et a, Predicting fluid responsiveness by passive leg raising: a systematic review and meta-analysis of 23 clinical trials., 2016, Journal : Critical care medicine.

Chan Gregory S H et al., "Automatic detection of left ventricular ejection time from a finger photoplethysmographic pulse oximetry waveform: comparison with Doppler aortic measurement," Physiological Measurement, vol. 28, No. 4, Mar. 20, 2007, pp. 1-14, Mar. 2007, Physiological Measurement, vol. 28, No. 4, Mar. 20, 2007, pp. 1-14.

Harley Alexander et al., "Pressure-Flow Studies in Man. An Evaluation of the Duration of the Phases of Systole," The Journal of Clinical Investigation, vol. 48, May 1, 1969, pp. 895-905, May 1969, The Journal of Clinical Investigation, vol. 48, May 1, 1969, pp. 895-905.

Murata Kazuhiko et al. "Alterations of Circulatory Responses to Upright Tilt in Cardiac Patients," Japanese Heart Journal, vol. 22, No. 4, Jul. 31, 1981, pp. 551-560, Jul. 1981, Japanese Heart Journal, vol. 22, No. 4, Jul. 31, 1981, pp. 551-560.

Stafford R. W. et al. "Left Ventricular Systolic Time Intervals as Indices of Postural Circulatory Stress in Man," Circulation, vol. 41, No. 3, Mar. 1, 1970, pp. 485-492, Mar. 1970, Circulation, vol. 41, No. 3, Mar. 1, 1970, pp. 485-492.

Hiroshi Kawamura "Sleep and Blood Pressure Variation—Merits and Demerits of REM Sleep," Journal of Clinical and Experimental Medicine (Igaku no ayumi), vol. 177, No. 9, Jun. 1, 1996, pp. 626-629, Jun. 1996, Journal of Clinical and Experimental Medicine (Igaku no ayumi), vol. 177, No. 9, Jun. 1, 1996, pp. 626-629.

\* cited by examiner

Blood Translocation with Position Change

Normal Cardiac Physiology

A. Effect of head-up tilt on the left ventricular pre-ejection period and ejection time in 15 normal subjects and in three patients with severe congestive heart failure. B. Effect of head-up tilt on the left ventricular pre-ejection period and ejection time in 15 normal subjects and in two patients restudied after diuresis.

Ring Sensor

Communication system with charging system for ring

OBSERVATIONAL HEART FAILURE MONITORING SYSTEM

CROSS-REFERENCE TO RELATED APPLICATIONS

This application is a national stage application under 35 U.S.C. 371 of PCT application PCT/US2016/065135, filed 2016 Dec. 6, which claims priority to U.S. provisional applications 62/263,839, filed 2015 Jul. 12, 62375431 filed 2016 Aug. 15, and 62423701 filed 2016 Nov. 17. Each of the foregoing is incorporated by reference herein.

BACKGROUND OF THE INVENTION

Heart failure occurs due to inadequate cardiac output. Management goals are thus focused on the optimization of stroke volume for the patient with limited cardiac function. Stroke volume is critically dependent on the volume of blood in the left ventricle at the end of diastole, the end diastolic volume. FIG. 1 is a graphical representation of patient with heart failure. The overall performance of the heart in a patient with heart failure is defined by decreased stroke volume when the end diastolic filling pressure exceeds an optimal level. Optimal performance of the heart occurs over a limited range of end diastolic pressures and is labeled "target volume" in the figure and is represented using Frank-Starling curve. Thus, fluid management in these patients is critical; too little fluid leads to decreases stroke volume while fluid overload also leads to decreased stroke volume.

Heart failure is a significant medical problem with an estimated US cost of approximately $30 billion annually with 80% of that expenditure being attributable to hospital admissions. The ability to reduce hospital admissions by improved ambulatory management has been a long-standing clinical objective. The primary cause of heart failure-related hospitalizations is fluid overload. Historical monitoring methods for fluid overload, such as shortness of breath, swelling, fatigue, and weight gain, are not sensitive enough to reflect early pathophysiologic changes that increase the risk of decompensation and subsequent admission to the hospital. Lewin J, Ledwidge M, O'Loughlin C, McNally C, McDonald K. Clinical deterioration in established heart failure: what is the value of BNP and weight gain in aiding diagnosis? Eur J Heart Fail. 2005; 7(6):953-957. Stevenson L, Perloff J K. The limited reliability of physical signs for estimating hemodynamics in chronic heart failure. JAMA. 1989; 261(6):884-888. FIG. 2 shows a typical clinical course of a heart failure patient with increasing fluid overload resulting in hospitalization. Examination of the figure shows that clinically observable signs occur late in the overall decompensation sequence. Thus, the use of clinical symptoms for the management of heart failure patients is problematic.

The difficulty of determining early hemodynamic congestion is demonstrated by the recently completed Better Effectiveness After Transition-Heart Failure (BEAT-HF) study. The study involving more than 1400 patients who were extensively monitored with existing noninvasive technology. The study investigated aggressive management of heart failure patients using a protocol that included pre-discharge heart-failure education, regularly scheduled telephone coaching, and telemonitoring. Telemonitoring included a Bluetooth-enabled weight scale and blood-pressure/heart-rate monitor integrated with a text device that sent the information to a centralized call center for review. If predetermined thresholds were exceeded, the patient was called and medication changed as determined by the clinical staff. Also, if significant symptoms were reported, the patient's heart-failure physician was notified and the patient was sent to the emergency department, if necessary. The conclusion from this extensive clinical study was no significant effect on hospital readmission rates.

Decreases in hospital admission rates have been demonstrated by using an invasive-implanted pulmonary artery pressure monitoring system. The CardioMEMS HF System measures and monitors the pulmonary artery (PA) pressure and heart rate in heart failure patients. The System consists of an implantable PA sensor, delivery system, and Patient Electronics System. The implantable sensor is permanently placed in the pulmonary artery, the blood vessel that moves blood from the heart to the lungs. The sensor is implanted during a right heart catheterization procedure. The Patient Electronics System includes the electronics unit and antenna. The Patient Electronics System wirelessly reads the PA pressure measurements from the sensor and then transmits the information to the doctor. After analyzing the information, the doctor may make medication changes to help treat the patient's heart failure. In a clinical study in which 550 participants had the device implanted, there was a clinically and statistically significant reduction in heart failure-related hospitalizations for the participants whose doctors had access to PA pressure data. The system costs approximately $2000 to implant and has a list price of $18,000.

SUMMARY OF INVENTION

The present invention is related to U.S. provisional applications 62/263,839, 62/375,431, and 62423701, each of which is incorporated herein by reference. Embodiments of the present invention address the limitations of current monitoring by providing a noninvasive, non-implanted, easy to use system for determination of cardiac function for the avoidance of hospital admissions due to fluid overload. Example embodiments make use of changes in venous return that occur due to body position changes during everyday activities. These changes are identified by the system via sensors that sense position, motion, or a combination thereof. In addition, pulse contour information is used for the assessment of cardiovascular function. Cardiovascular function assessment is made on a personalized basis, and thus is insensitive to between-subject differences such as height, weight, age, and fitness level. The resulting cardiovascular assessment is subsequently evaluated so that the heart failure patient can be managed in a proactive manner for the avoidance of fluid overload and possible admission to the hospital. Example embodiments use an optical measure of the pulse, e.g., a photoplethysmogram (PPG), obtained from a wearable device for the determination of cardiovascular function. The PPG can be obtained from many locations in the body; in some example embodiments, it is convenient to use PPG signals derived from a watch located on a wrist or from a ring located at the base of a finger. The resulting pulse contour data can be processed in conjunction with body position information for the determination of cardiovascular function. Cardiovascular function information can then be evaluated as a function of time, as a function of body position, or a combination thereof, to determine impairment indicative of hemodynamic congestion. The system acquires the data for cardiovascular assessment in an observational manner and does not typically require the patient to perform specific testing protocols or prescribed rituals. If the system lacks critical data associated with making an accurate assessment, the patient can be asked to address these data limitations by adjusting the location of the sensor or by performing a sequence of movements. The system can be implemented with noninvasive sensors, so the risk and cost disadvantages attendant with implanted sensors are avoided.

DESCRIPTION OF THE INVENTION

Figure 1:
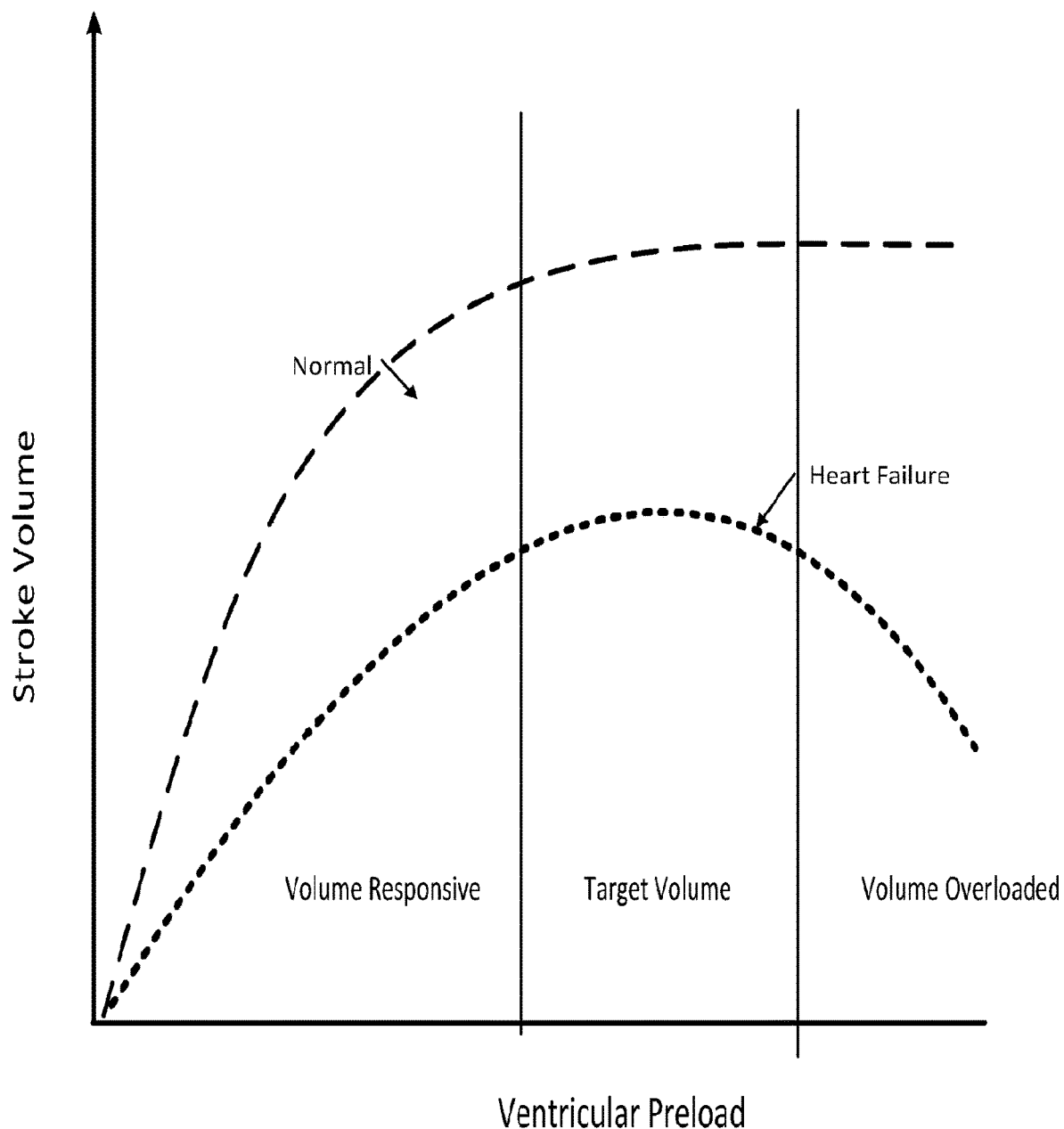
FIG. 1 is a schematic representation of the Frank Starling Curve.
Figure 2:
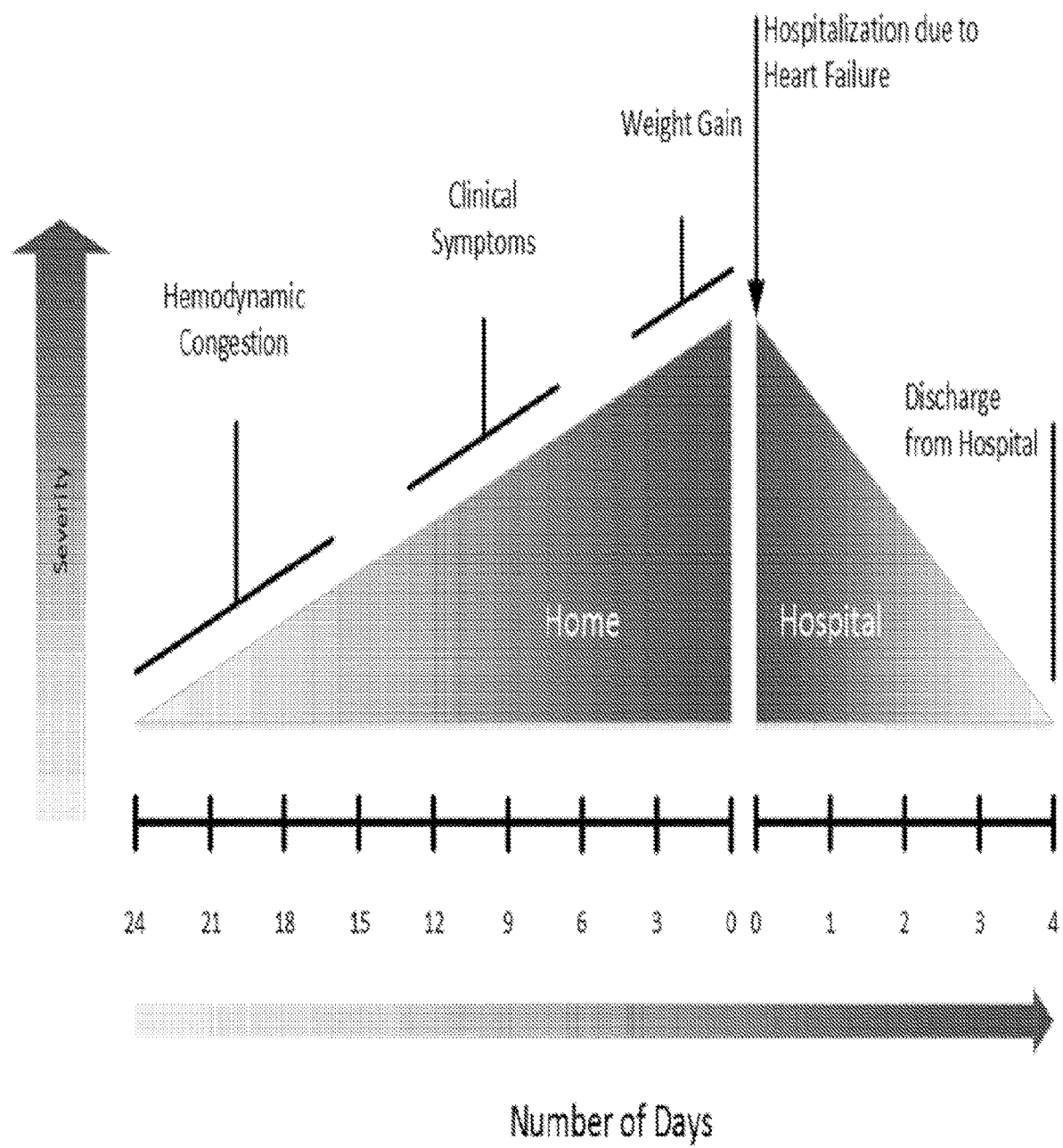
FIG. 2 is a schematic representation of hemodynamic congestion over time.

Embodiments of the present invention provide methods and apparatuses for the assessment of cardiovascular function in an ambulatory heart failure patient. Embodiments use pulse contour data obtained by wearable PPG sensors for the determination of cardiovascular function metrics in the presence of body position changes. Body position changes are inferred by sensors that sense position, motion, or a combination thereof. In operation of example embodiments, the measurement process is entirely observational in nature and does not require the patient to conduct a specific test, perform a defined activity, or be subject to any invasive measurement.

Due to the etiology of heart failure, changes in cardiovascular function are typically associated with changes in overall fluid status which directly influence the pulse contour. Specific changes in the pulse contour are the result of hemodynamic congestion, commonly referred to as fluid overload. The ability to continuously monitor overall cardiac function in the ambulatory heart failure patient provides the opportunity for improved care, optimization of medical management, and the avoidance of hospital admissions. The resulting system for the first time recognizes an application of current wireless and gesture recognition technology to be combined with historical physiological observations of heart failure.

Definitions

As used herein, "volume assessment" includes but is not limited to the general assessment of volume in the human body including intravascular volume, extra vascular volume, dehydration, total body water, extracellular volume, and plasma volume. In medicine, intravascular volume status refers to the volume of blood in a patient's circulatory system, and is essentially the blood plasma component of the overall volume status of the body, which otherwise includes both intracellular fluid and extracellular fluid. The intravascular component is usually of primary interest, and volume status is sometimes used synonymously with intravascular volume status.

Hemodynamic congestion is defined as increased left ventricular filling, or intravascular pressures and decreased stroke volume, or a combination thereof. The Frank-Starling law of the heart (also known as Starling's law or the Frank-Starling mechanism or Maestrini heart's law) states that the stroke volume of the healthy heart increases in response to an increase in the volume of blood filling the heart (the end diastolic volume) when all other factors remain constant. In a healthy heart, a larger volume of blood flowing into the ventricle stretches the walls of the heart, causing a greater expansion during diastole. This in turn increases the force of the contraction during systole and thus the quantity of blood that is pumped into the aorta. In the failing heart, the Frank-Starling mechanism is exhausted, i.e. the failing heart operates at or close to the maximum of the Frank-Starling curve. In this case, enhanced preload leads to a lack of change, or a decrease in stroke volume.

End-diastolic volume (EDV) is the volume of blood in the right and/or left ventricle at the end of filling (diastole), or the amount of blood in the ventricles just before systole. End-diastolic volume is often used synonymously with preload.

As used herein, photoplethysmography (PPG) is an optical measurement technique that can be used to detect blood volume changes in tissue or has a signal that is related to the cardiac cycle.

Positional changes or changes in pose are general terms that applies to any process that changes the overall venous return to the heart. Common body positions include supine, sitting and standing.

The term "signal" as used herein includes any means of transmitting information such as a measurement, including without limitation an analog electrical waveform or digital representation thereof, which is collected or transmitted by a biological or physiological sensor, such as a PPG.

The pulse contour describes the shape of the pulse waveform. The peripheral pulse waveform reflects a summation of the primary wave and secondary waves that arise from the closure of the aortic valve and various reflections in the vascular tree. Changes in volume status, venous return, body position, and stroke volume impact the size and timing of these secondary waves relative to the primary wave. Thus, pulse contour analysis can be used for cardiac function assessment. There are various pulse waveform quantification methods which include frequency analysis, wavelet transformation, decomposition methods and curve fitting. An example curve fitting approach uses a mixture of Gaussians which capture the relative timing and amplitude of primary and secondary pulse waves.

A body position assessment system comprises a sensor or sensors that enable detection of body position change. The system can be attached to the patient or can observe the patient from an unattached position, or a combination thereof.

The pulse detection system comprises a sensor or sensors that enable the measurement of a pulse waveform. Examples include optical sensors, commonly referred as pulse PPG, and can be used on various locations on the body including one or more fingers, one or more ears, one or more wrists, chest, or forehead. Pulse detection systems can include image based systems that determine pulse waveforms by optical imaging. Other methods include any technique that can be used to detect blood volume changes in tissue or has a signal that is related to the cardiac cycle. In addition to the PPG-based methods, laser Doppler probes, tonometers and pulse transducers can be used to acquire signals related to the cardiac cycle. Typical pulse transducers use a piezo-electric element to convert force applied to the active surface of the transducer into an electrical analog signal that is related to the cardiac cycle.

The term "pre-ejection period" (PEP) as used herein, is the time from the onset of ventricular depolarization to the opening of the aortic valve during the cardiac cycle.

The term "left ventricular ejection time" (LVET) as used herein, is the time of ejection of blood from the left ventricle beginning with aortic valve opening and ending with aortic valve closure Cardiac function assessment is an assessment of cardiac function based upon information received for the pulse contour of a PPG signal. Cardiac function assessment can include LVET measurements made by detection of the primary pulse wave and the detection of the incisura. Cardiac function assessment can also include additional evaluation metrics, used singularly or in combination, to include but not limited to pre-ejection period, pulse amplitude, heart rate variability, heart rate, respiratory rate, or other decompositions of the pulse contour.

DETAILED DESCRIPTION OF THE INVENTION

Physiology of Position Changes in Normal Hearts

The characteristics of the cardiovascular system that are used by the invention are described to facilitate understanding of the invention. While the cardiovascular system has been studied for years, the combination of characteristics and measurements described herein has not been previously described.

Figure 3:
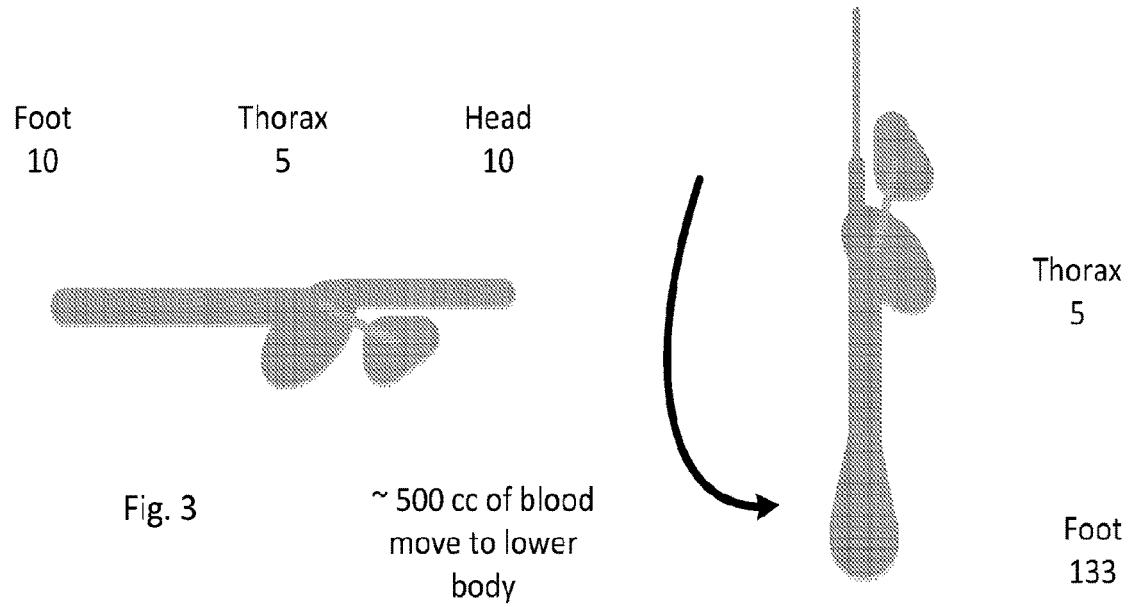
FIG. 3 is a schematic illustration of the translocation of blood due to position changes.

Moving from the supine to upright posture results in the translocation of 300 to 800 cc of blood from the central intravascular compartment to dependent regions in the legs, buttocks, pelvis, and splanchnic circulation. FIG. 3 is an illustration of blood translocation due to position change. The figure shows changes in venous blood volume (shaded area) as the patient moves from supine position to standing. The thoracic compartment includes the central veins, heart and pulmonary blood; the lungs are shown disproportionately small. Numbers are typical pressures in cmH20. figure modified from er Gauer, O. H. and Thron, H. L. (1963) Handbook of Physiology, Circulation, Vol. 3 (eds. W. F. Hamilton and P. Dow, American Physiological Society, Bethesda, pp. 2409-2440. The volume of blood moved is dependent upon patient specific characteristics to include leg length, leg size and muscle mass. In a patient with normal cardiovascular function, this orthostatic stress evokes a sequence of compensatory cardiovascular responses to maintain homeostasis.

Figure 4:
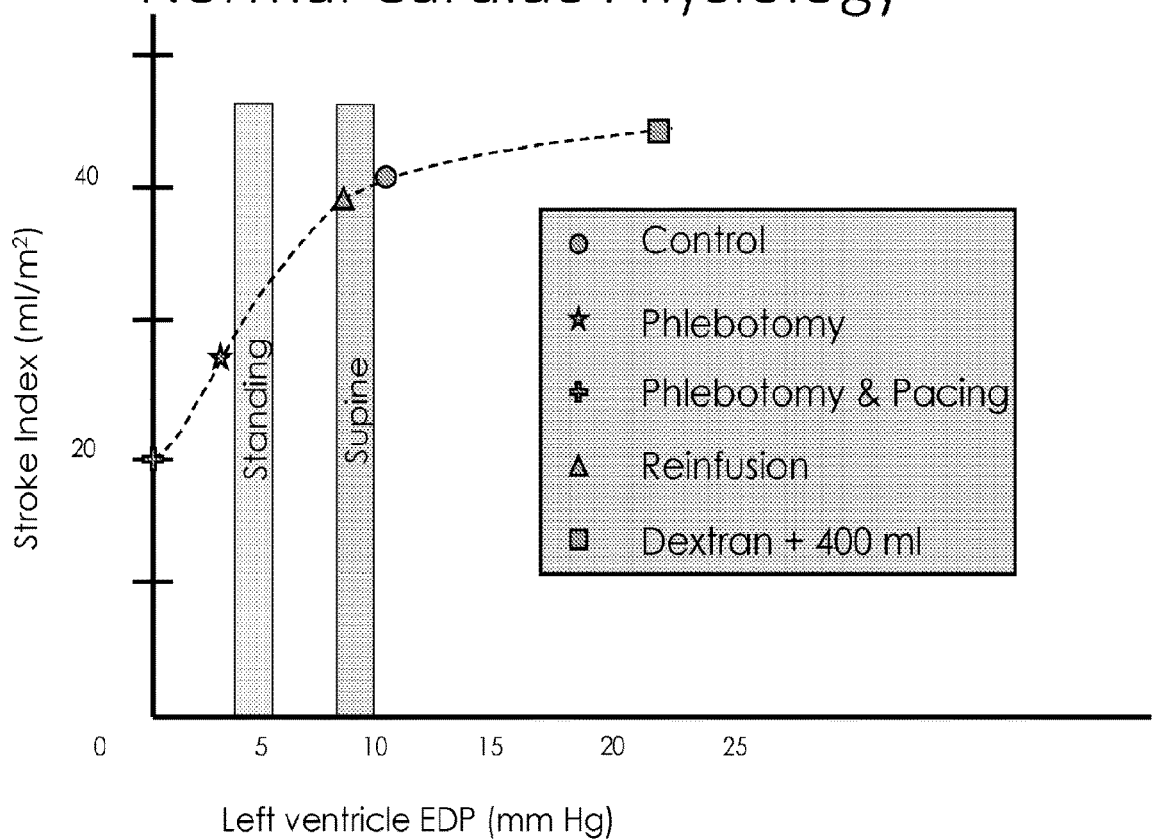
FIG. 4 is a schematic representation of a normal response to body position change.

The normal response to a positional change from supine to standing is represented on the Frank-Starling curve as shown in FIG. 4 reproduced from Levick, J. Rodney. An introduction to cardiovascular physiology. Butterworth-Heinemann, 2013, page 71. The figure demonstrates several key physiological points: (1) body position changes alter venous return to the heart and causes a change in left ventricle end diastolic pressure (x-axis), and (2) the change in end diastolic pressure has a significant impact on cardiac output or stroke volume (y-axis). The plot illustrates the marked change in cardiac function as measured by stroke volume due to a change in position from standing to laying down. The plot also shows the effect of volume overload by infusing 400 ml of dextran. With increased fluid or fluid overload, cardiac function as defined by stroke volume begins to reach a maximum in the normal heart.

Physiology of Position Changes in Heart Failure

As shown in FIG. 1, the response of the diseased heart to changes in end diastolic pressure is different than the normal heart. Murata et al. examined cardiac function response to positional changes by using an upright tilt test in normal patients and in cardiac patients. In normal patients, the upright tilt causes an increase in heart rate and diastolic pressure, a slight decrease in systolic pressure and a marked decrease in cardiac output and stroke volume. The response to tilt was less pronounced in the cardiac patients as compared with the normal patients. In particular, the reduction in the cardiac output was significantly diminished. In fact, a paradoxical increase in cardiac output during the tilt was observed in those cardiac patients with the lowest cardiac output. The work of Murata et al demonstrates an altered response to positional changes in those patients with heart failure. The measurements used by Murata et al. were not made using a PPG but were made using a phonocardiogram for a microphone placed in the second intercostal space, an EKG, with cardiac output assessed via right carotid arteriogram. An arteriogram is an imaging test that uses x-rays and a special dye to see inside the arteries. It can be used to view arteries in the heart, brain, kidney, and other parts of the body. Murata, Kazuhiko, et al. "Alterations of circulatory responses to upright tilt in cardiac patients." Japanese heart journal 22.4 (1981): 551-560.

Abelmann et al. conducted similar testing in 1969 and demonstrated that patients with heart disease have a decreased response to upright tilting. Testing involved placing patients on a tilt table with the patient resting for 30 minutes in the horizontal position. The patient was then manually tilted up within three seconds to a 70° head-up position. The authors describe a heart failure response characterized by the absence of changes in pulse pressure, diastolic pressure, and heart rate. The authors state that the decreased positional response is due to increased venous pressure and blood volume. The authors confirmed this hypothesized mechanism by conducting positional changes on healthy patients after acute volume expansion or depletion of blood volume. Abelmann, Walter H., and Khaja Fareeduddin. "Increased tolerance of orthostatic stress in patients with heart disease." The American journal of cardiology 23.3 (1969): 354-363.

Figure 5:
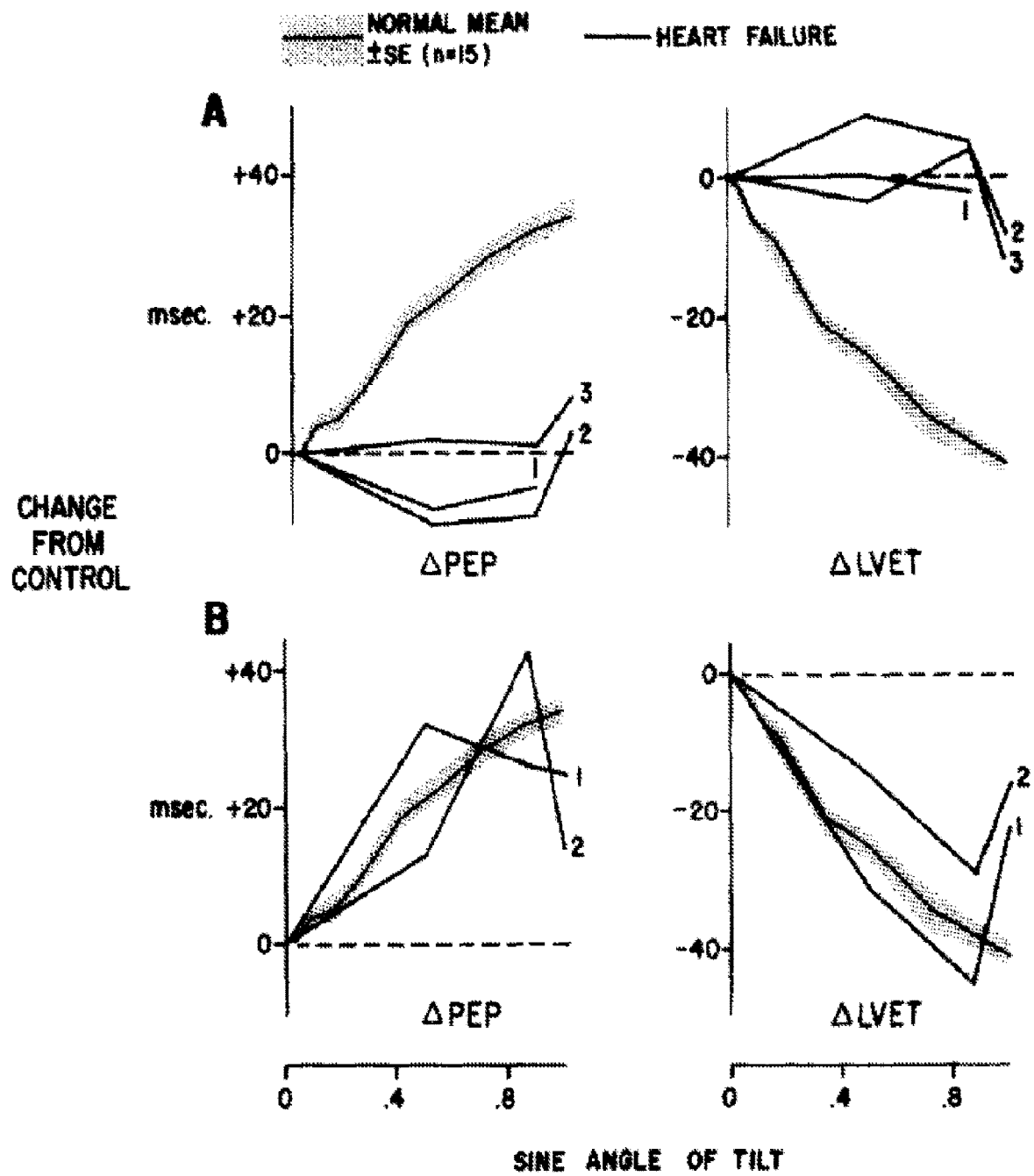
FIG. 5 is a demonstration of a CHF response to body position change.

Stafford et al. in 1970 demonstrated that the lack of positional response in heart failure patients can be reversed by diuresis (fluid removal from the patient). The authors show that, in contrast to the normal patients, patients with congestive heart failure demonstrated little change in cardiac function during head-up tilt. However, following diuresis, the response of the heart failure patients returned to normal. The publication by Stafford assesses cardiac function by using systolic time intervals including pre-ejection period and left ventricular ejection time. Their results, reproduced as FIG. 5 here, show changes in left ventricular ejection time as a function of tilt for both normal patients and those with heart failure. Stafford, R. W., W. S. Harris, and A. M. Weissler. "Left ventricular systolic time intervals as indices of postural circulatory stress in man." Circulation 41.3 (1970): 485-492.

The above publications demonstrate a critical linkage between increased fluid status and a lack of cardiac function response to positional changes. The inventors have recognized that positional changes can be useful for the general assessment of cardiovascular function in patients with heart failure. Additionally, the Stafford paper demonstrates that normalization of fluid status results in a return of cardiovascular variability (FIG. 5B). The current invention contemplates these physiological observations, and provides a heart failure assessment method that uses the activities of daily living and their associated venous return changes. Cardiac function can be assessed during these activities by a noninvasive, wearable system that measures pulse contours.

Measurement of Incisura

The invention provides a system that can be used by a patient for the monitoring of heart failure. PPG measurements provide a measurement approach that is noninvasive, low-cost and wearable. In previous applications of PPG measurements, such as heart rate monitoring or pulse oximetry, the sampling rate of the system is too low to create a pulse contour that can be used for cardiac function analysis. The current invention acquires PPG signals with a sampling frequency that enables a high-resolution evaluation of the pulse contour.

Figure 6:
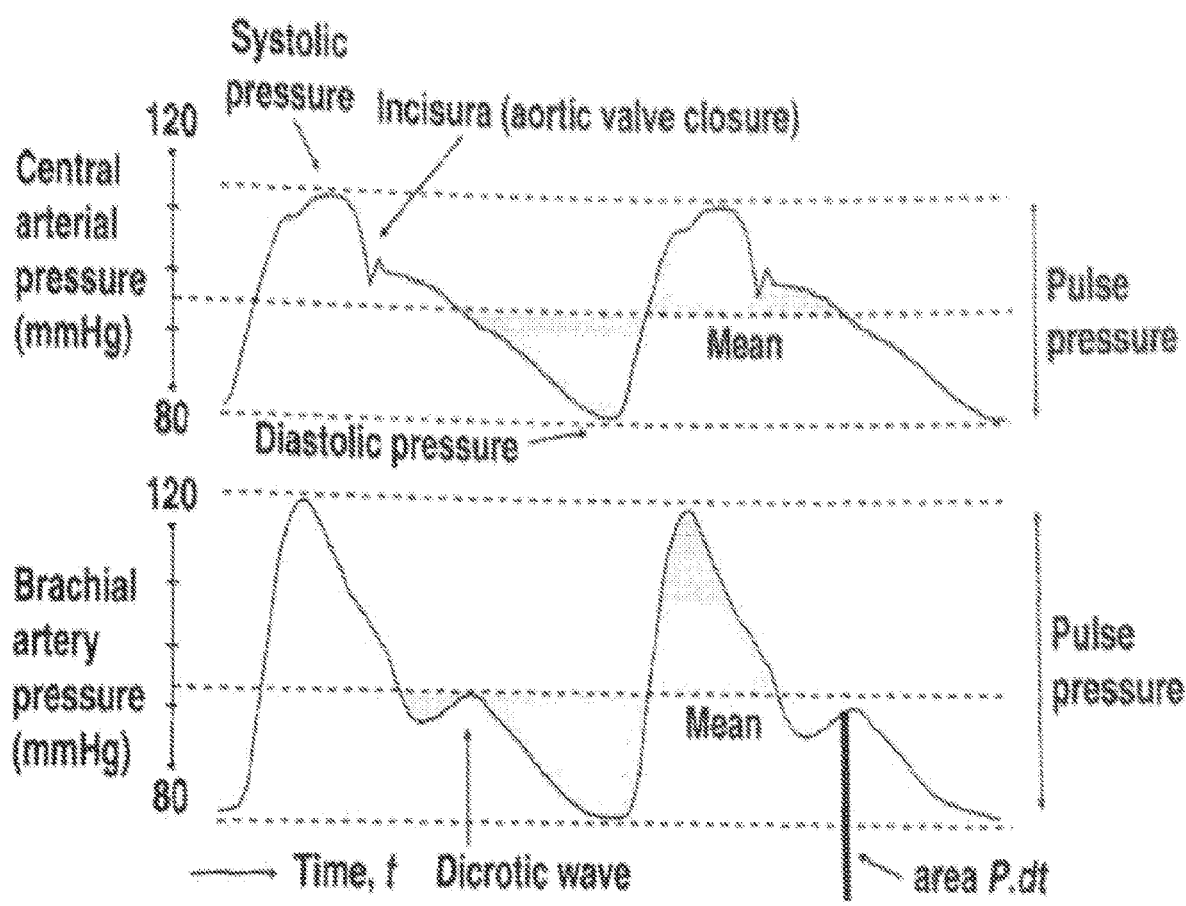
FIG. 6 is a representation of incisura in central and peripheral vessels.

The system detects the incisura point in the PPG signal. The incisura is the notch in the pressure or volume trace produced by aortic value closure. The closure of the aortic value creates a momentary stoppage and slight reversal of flow at the aortic value. This change in flow creates a central pressure change and creates an incisura. The incisura is transformed as it propagates to the periphery due to dampening in the arterial system, but remains a valid time marker for aortic closure. The transformation of the waveform can be appreciated by examining FIG. 6, reproduced from Levick, Cardiovascular Physiology, 5th ed., 2010, which shows the pressure pulse waveform at the central subclavian artery and in the peripheral brachial artery. Due to physiological differences between people in vascular morphology and stiffness, incisura will be transformed differently, but can be detected with PPG and serves as a marker for aortic closure.

Cardiac Function Parameters

Figure 7:
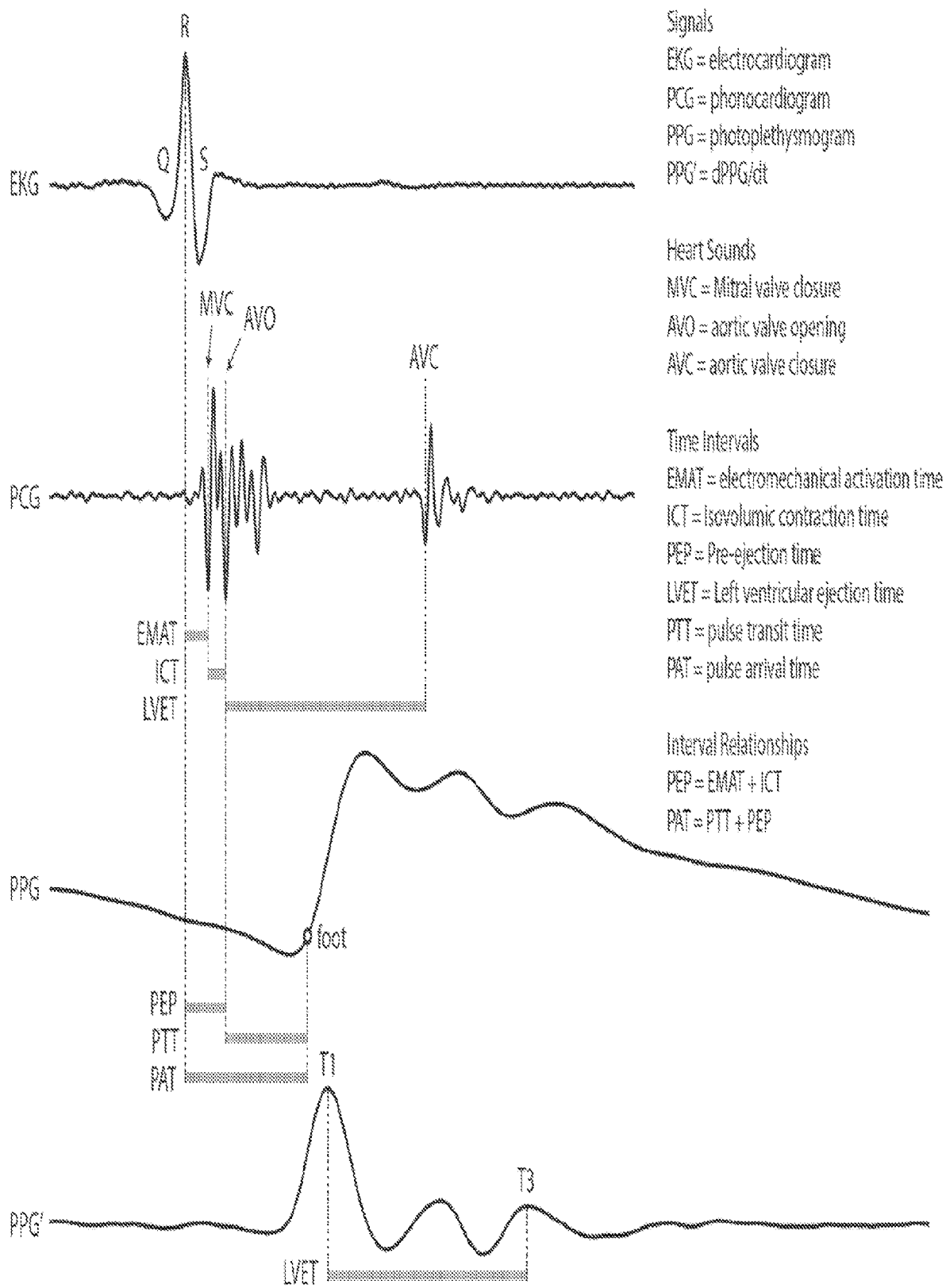
FIG. 7 illustrates the relationship between measured cardiac parameters.

The left ventricular ejection time (LVET) is an example of a cardiac parameter that can be determined from a PPG signal by examination of the primary wave and the incisura. LVET defines the duration of ventricular ejection, i.e., from the aortic valve opening (AVO) to the aortic valve closure (AVC). LVET can be determined from PPG pulse waveforms recorded at peripheral sites such as the finger, wrist, or the ear. As shown by Quarry-Pigott et al., and later by Chan et al., careful analysis of the derivative PPG waveform can identify transition points or peaks that correspond to the opening and closing of the aortic valve. Quarry-Pigott, Veronica, Raul Chirife, and David H. Spodick. "Ejection Time by Ear Densitogram and Its Derivative." Circulation 48.2 (1973): 239-246. Chan, Gregory S H, et al. "Automatic detection of left ventricular ejection time from a finger photoplethysmographic pulse oximetry waveform: comparison with Doppler aortic measurement." Physiological measurement 28.4 (2007): 439. In one approach, shown in FIG. 7, LVET is defined as the interval between the first and third peaks in the first derivative of the PPG waveform. In an alternative approach, LVET is defined as the interval between the first and third peaks in the third derivative of the PPG waveform.

The LVET allows for assessment of cardiac function. LVET is directly related to stroke volume, with larger stroke volumes lengthening LVET. The relationship between LVET and stroke volume was demonstrated by Weissler et al. In 1963, Weissler et al. investigated the volume sensitivity of LVET (and its heart rate corrected index, LVETI) and showed a significant reduction of LVETI during head up tilt, which reduces venous return and stroke volume. Weissler, Arnold M., Leonard C. Harris, and George D. White. "Left ventricular ejection time index in man." Journal of applied physiology 18.5 (1963): 919-923. The authors stated that "a fall in stroke volume (and therefore cardiac output) is reflected in a decrease in left ventricular ejection time and hence a diminution in the ejection time index." As LVET is also affected by heart rate (HR), with faster heart rates reducing LVET. Weissler et al suggest the use of the left ventricular ejection time index (LVETI), which is computed as LVETI=1.6×HR+LVET, where HR is the heart rate in beats/min. Any hemodynamic assessments based on LVET can also be based on the heart rate corrected index, LVETI.

In cardiovascular physiology, stroke volume (SV) is the volume of blood pumped from the left ventricle per beat. Stroke volume is calculated using measurements of ventricular volume from an echocardiogram and subtracting the volume of the blood in the ventricle at the end of a beat (called end-systolic volume) from the volume of blood just prior to the beat (called end-diastolic volume). The term stroke volume can apply to each of the two ventricles of the heart, although it usually refers to the left ventricle. In clinical practice, stroke volume is measured by invasive catheter systems or by echocardiography. As communicated above in the studies by Stafford and Weissler, the LVET period is a good surrogate for stroke volume. The work by Harley et al. showed a close and direct linear relationship between the duration of ejection and stroke volume. Harley, Alexander, C. Frank Starmer, and Joseph C. Greenfield Jr. "Pressure-flow studies in man. An evaluation of the duration of the phases of systole." *Journal of Clinical Investigation* 48.5 (1969): 895.

Cardiac Function Assessment by PPG and Body Position

Figure 8:
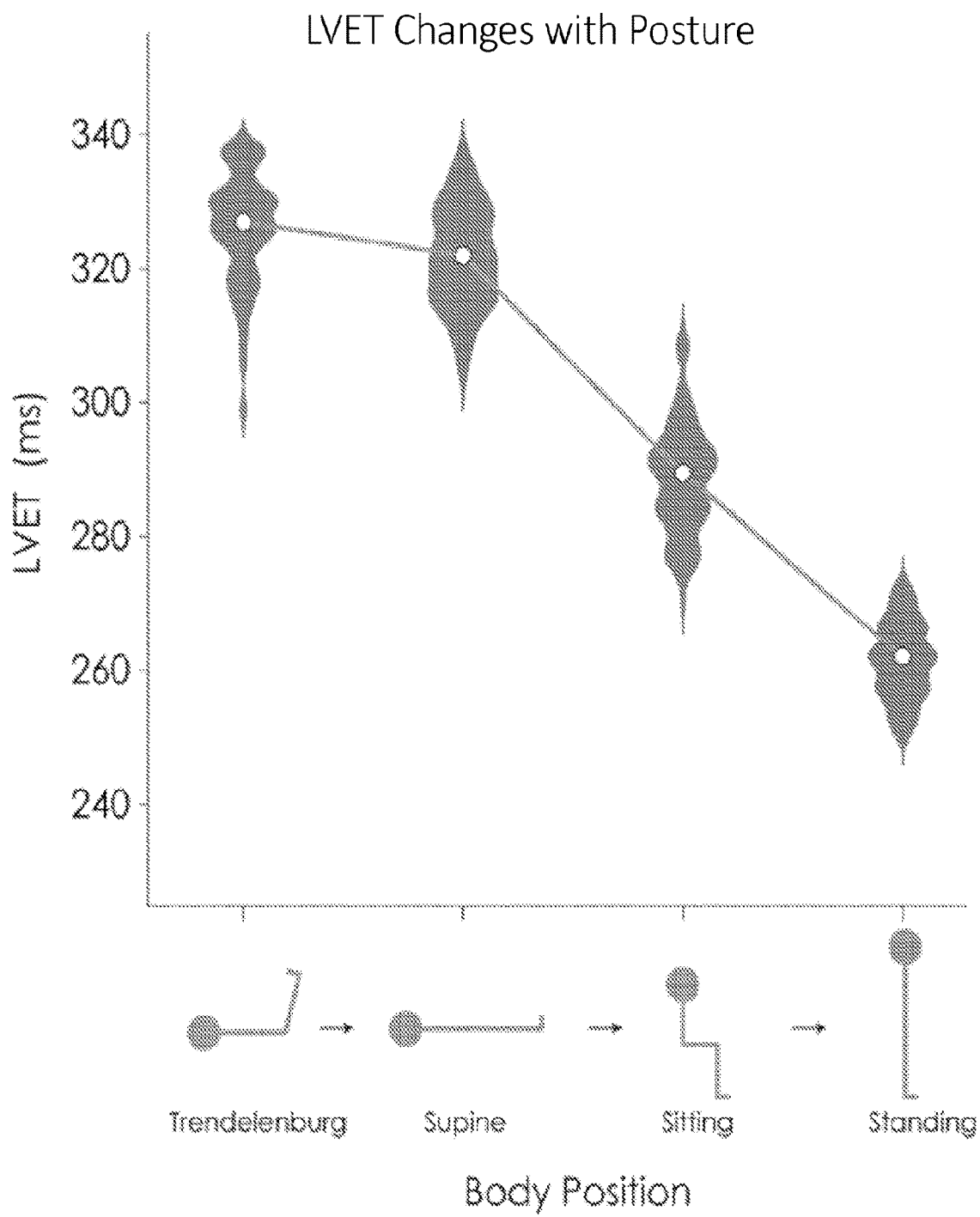
FIG. 8 is a plot of invention-derived LVET changes during body position changes.
Figure 9:
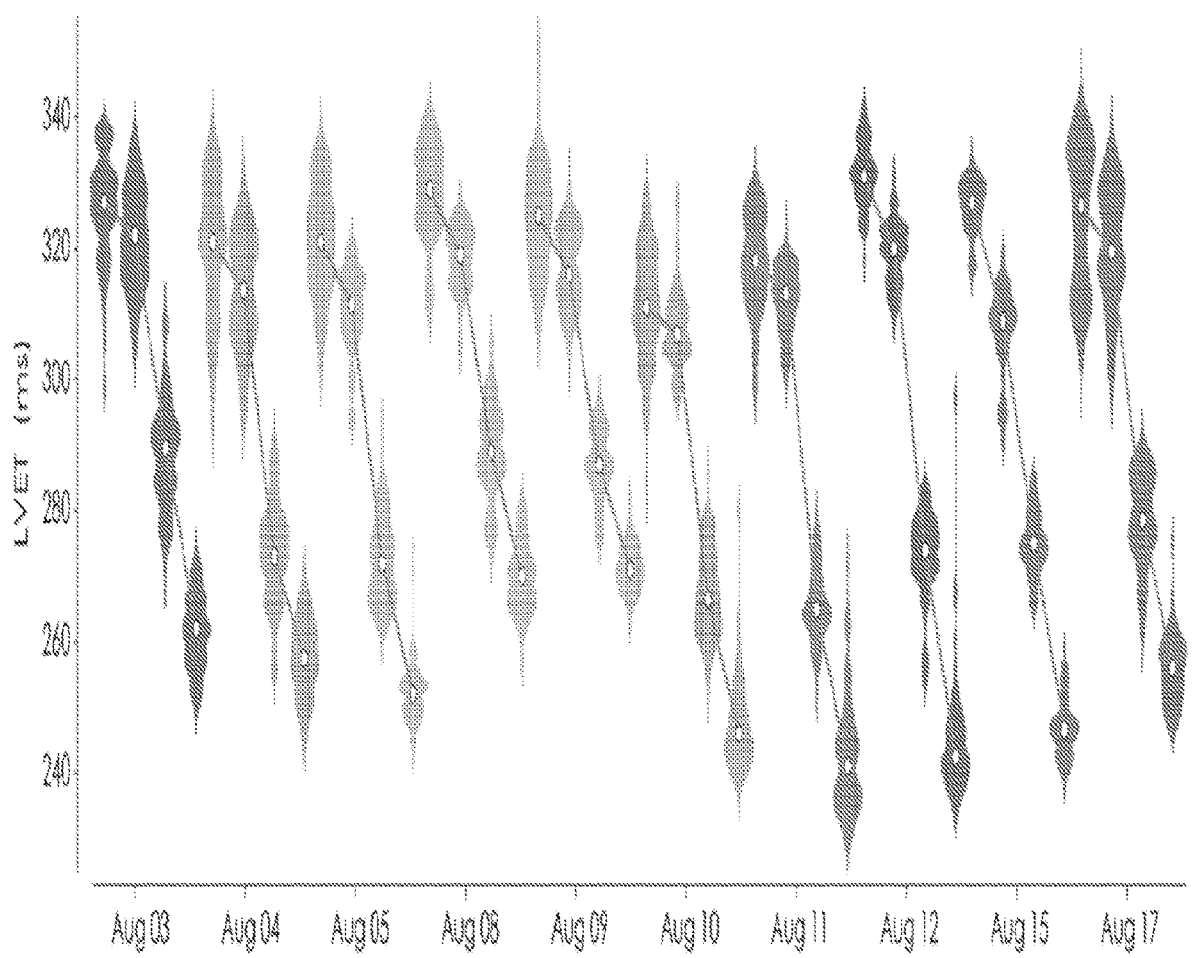
FIG. 9 is a plot of invention-derived LVET changes during body position changes over time.

The invention combines the determination of cardiac function parameters derived from pulse contours and the modification of venous return by changes in body position to assess hemodynamic status. Embodiments of the present invention combine these concepts into a usable system as demonstrated in FIG. 8 and FIG. 9. In this example, the examined patient was a 23-year-old male with no existing heart disease and PPG measurements were made with the distal end of the finger. The patient was asked to assume four different body positions in sequence, maintaining each position for 1 minute: 1) laying on a table with feet raised, 2) laying supine, 3) sitting, and 4) standing. This movement sequence creates a progressive decrease in venous return and hence stroke volume. FIG. 8 shows the distribution and median of LVET measurements made at each body position using a violin plot. Examination of the plot shows decreases in LVET between each position, particularly during the transitions from supine to sitting and sitting to standing. FIG. 9 shows the results of the same measurement protocol repeated multiple times over approximately 2 weeks. Examination of the figure shows that the LVET changes due to body position are robust and stable.

Figure 10:
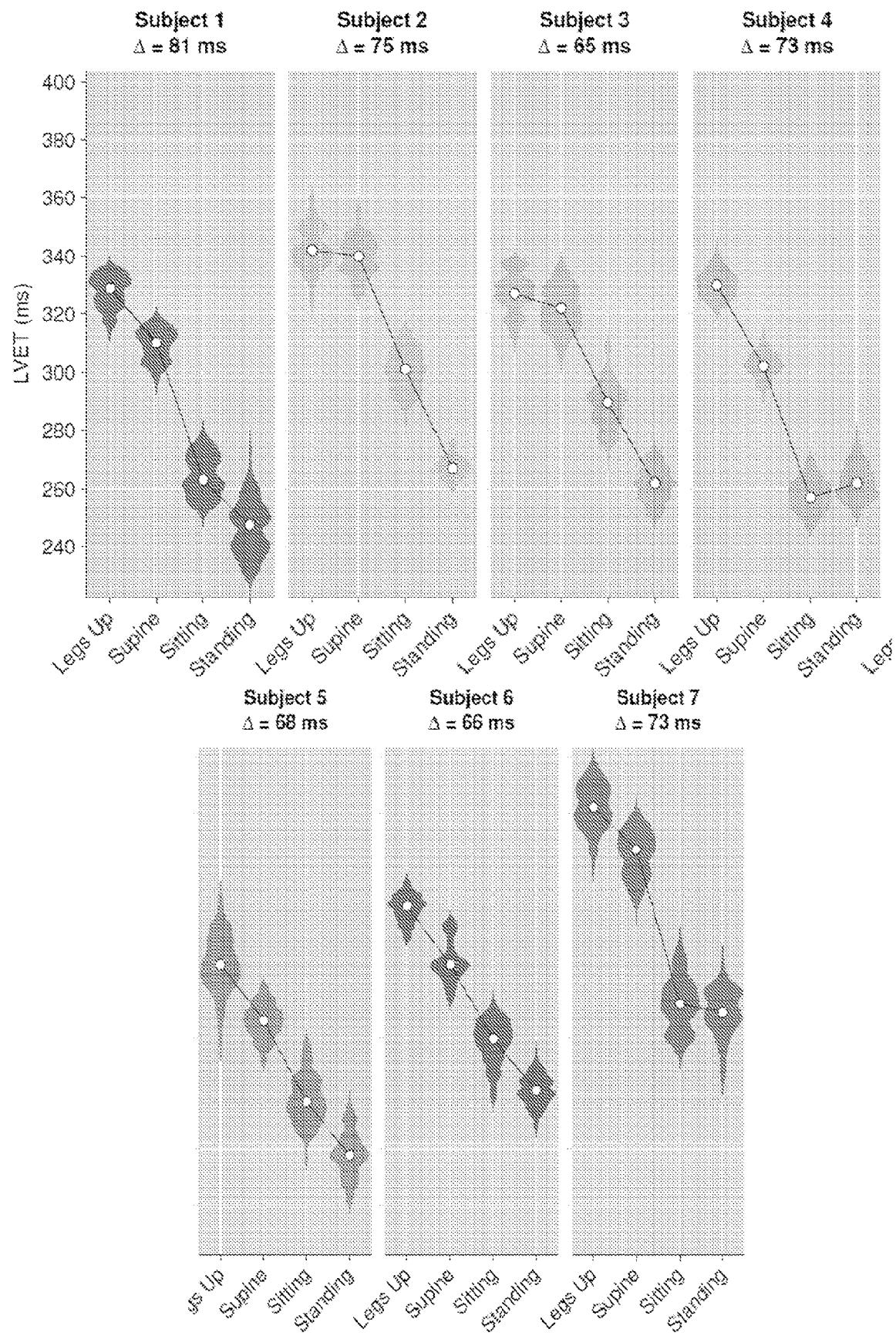
FIG. 10 is a plot comparing LVET changes due to body position changes between patients.

The physical characteristics, activity level, and overall health of the patient will influence baseline stroke volume and change in venous return due to position changes. The transition to a standing position results in a translocation of blood that varies between 300 to 800 cc from the central intravascular compartment to dependent regions in the legs, buttocks, pelvis, and splanchnic circulation. Embodiments of the present invention can mitigate this variance problem by using a personalized assessment system. Example embodiments make a heart failure evaluation based upon prior information acquired on each patient, resulting in a personalized assessment. FIG. 10 shows the response to changes in body position for seven individuals. PPG measurements were made with the distal end of the finger. The individuals examined were (Subject 1) 52-year-old male, height 5'8" with no known medical problems, (Subject 2) 38-year-old male, height 6'3" with no known medical problems, (Subject 3) 23-year-old male, height 5'6" with no known medical problems, (Subject 4) 77-year-old male, height 5'9" with compensated heart failure, (Subject 5) 47-year-old female, height 5'0" with no known medical problems, (Subject 6) 55-year-old female, height 5'6", with type 2 diabetes, (Subject 7) 19-year-old female, height 5'0" with no known medical problems. Although all subjects show a change in LVET of greater than 65 ms, some show changes as large as 80 ms, and the range in supine LVET between subjects exceeds 50 ms, more than twice the range observed in a single individual (FIG. 9). This increased variance between subjects demonstrates that the invention's personalized assessment of cardiac function will result in improved sensitivity.

Cardiac Function Assessment by PPG

Figure 11:
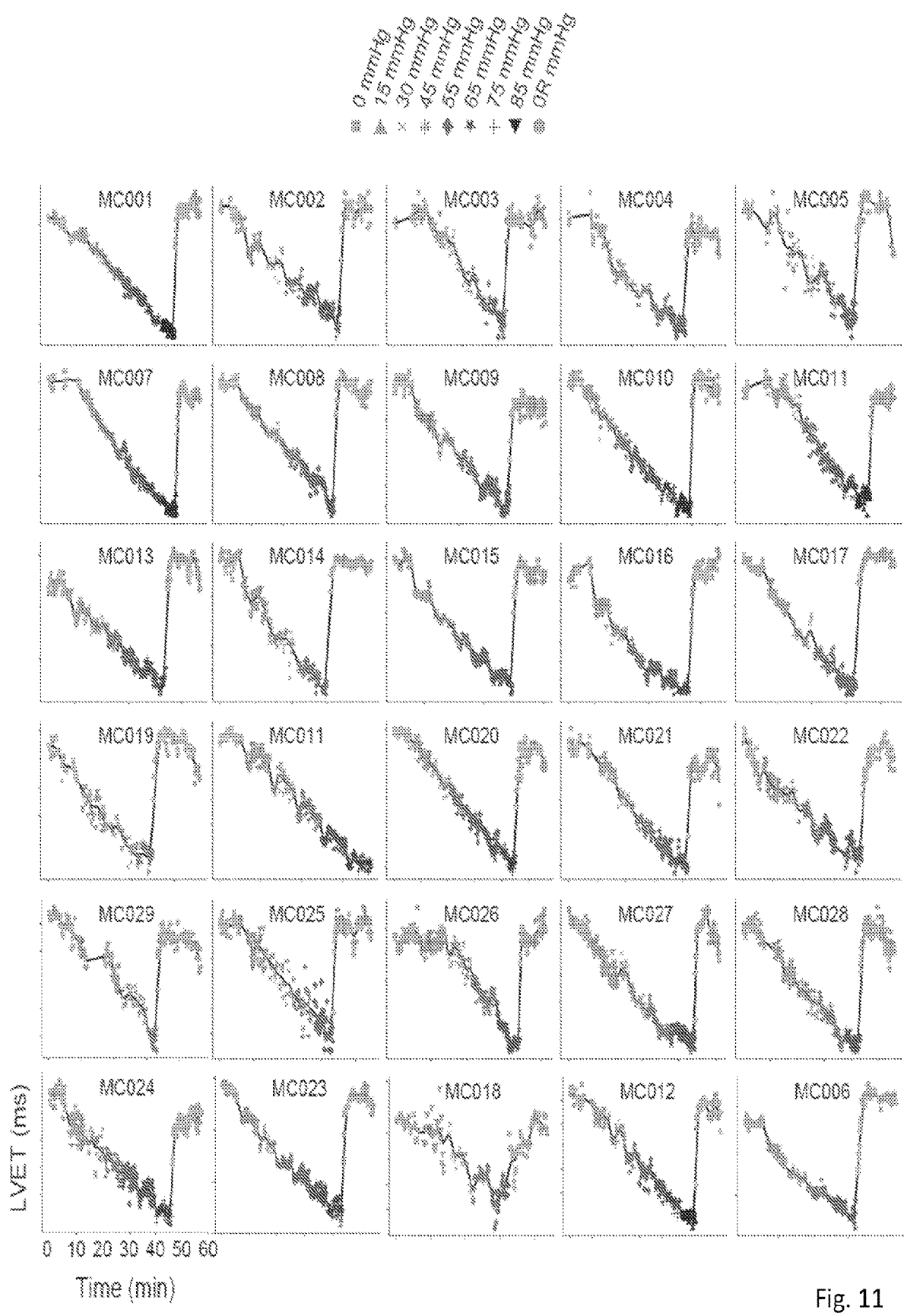
FIG. 11 is a plot of invention-derived LVET changes versus lower body negative pressure.
Figure 12:
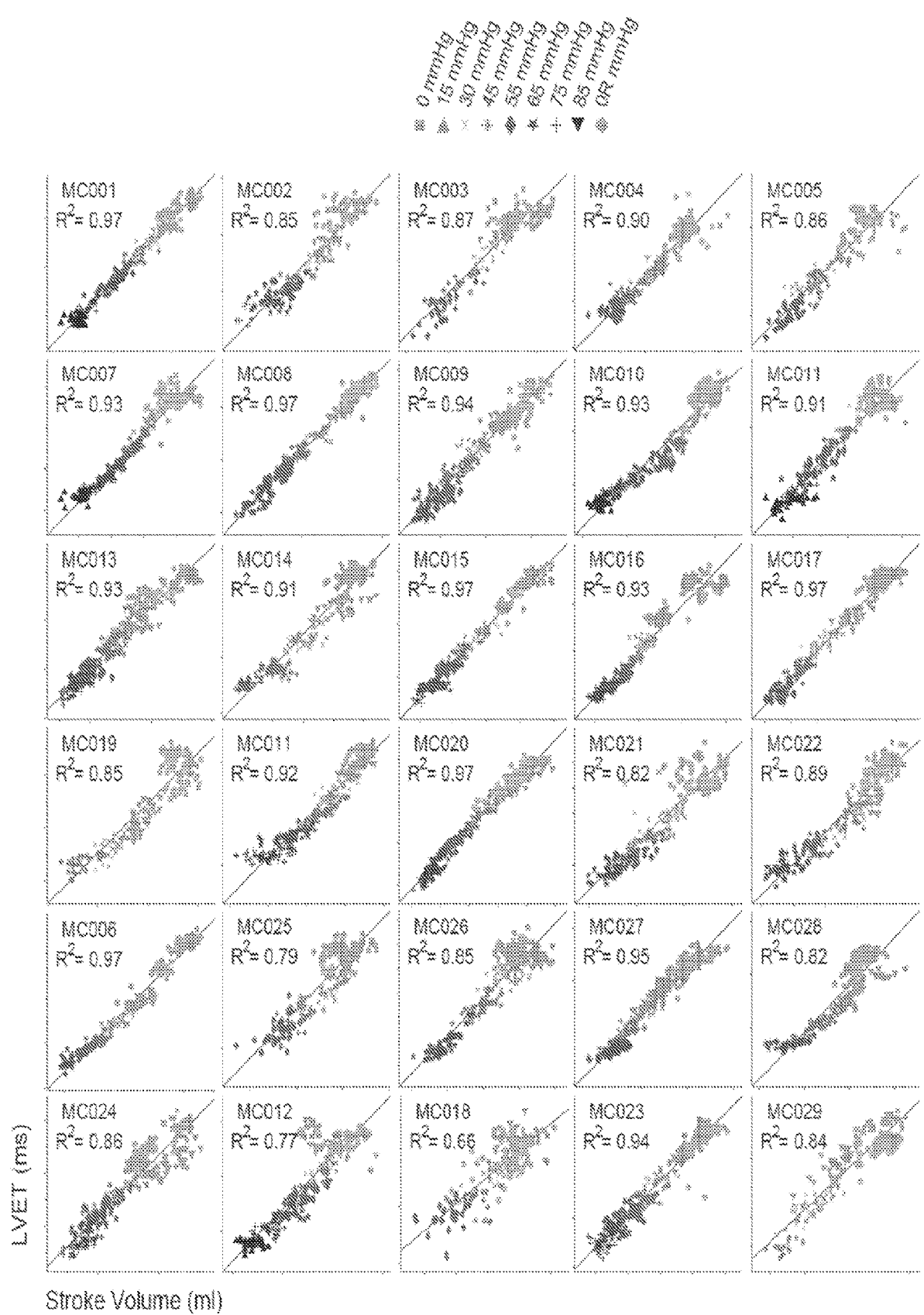
FIG. 12 is a plot of invention-derived LVET changes versus stroke volume.

With an objective of demonstrating cardiac function measurements by using PPG signal as contemplated by the present invention, a clinical study with 29 subjects was conducted where venous return was modified by using lower body negative pressure (LBNP). LBNP testing places the lower extremity of the patient in an air-tight chamber. A vacuum is connected and negative pressure generated. The negative pressure translocates blood into the lower body, substantially decreasing circulating volume and hence stoke volume. Applying LBNP is similar in nature to movement in blood that occurs as an individual stands up, though the magnitude of translocated blood can be much greater. In the LBNP testing protocol, negative pressure was increased until the subject developed pre-syncopal symptoms or experienced hypotension, whereupon the negative pressure was released and subject physiology normalized. The 29 subjects ranged in range from 21 to 65 years (median: 40 years) and included 13 females. PPG measurements were made with the distal end of the finger. FIG. 11 shows the results for 30 LBNP protocols performed. Examination of the figure shows systematic changes in LVET over time as the LBNP level was increased (denoted by symbols). The system also shows a fast response during the recovery phase of the study (denoted as OR mmHg). FIG. 12 shows the same LVET values from the same experiment plotted against stroke volume as determined by a Finometer (a clinically validated and FDA-approved reference system for determining stroke volume). Together, these figures show that PPG-derived LVET measurements are highly sensitive to changes in venous return, and that the LVET measurements faithfully reflect changes in stroke volume.

Figure 13:
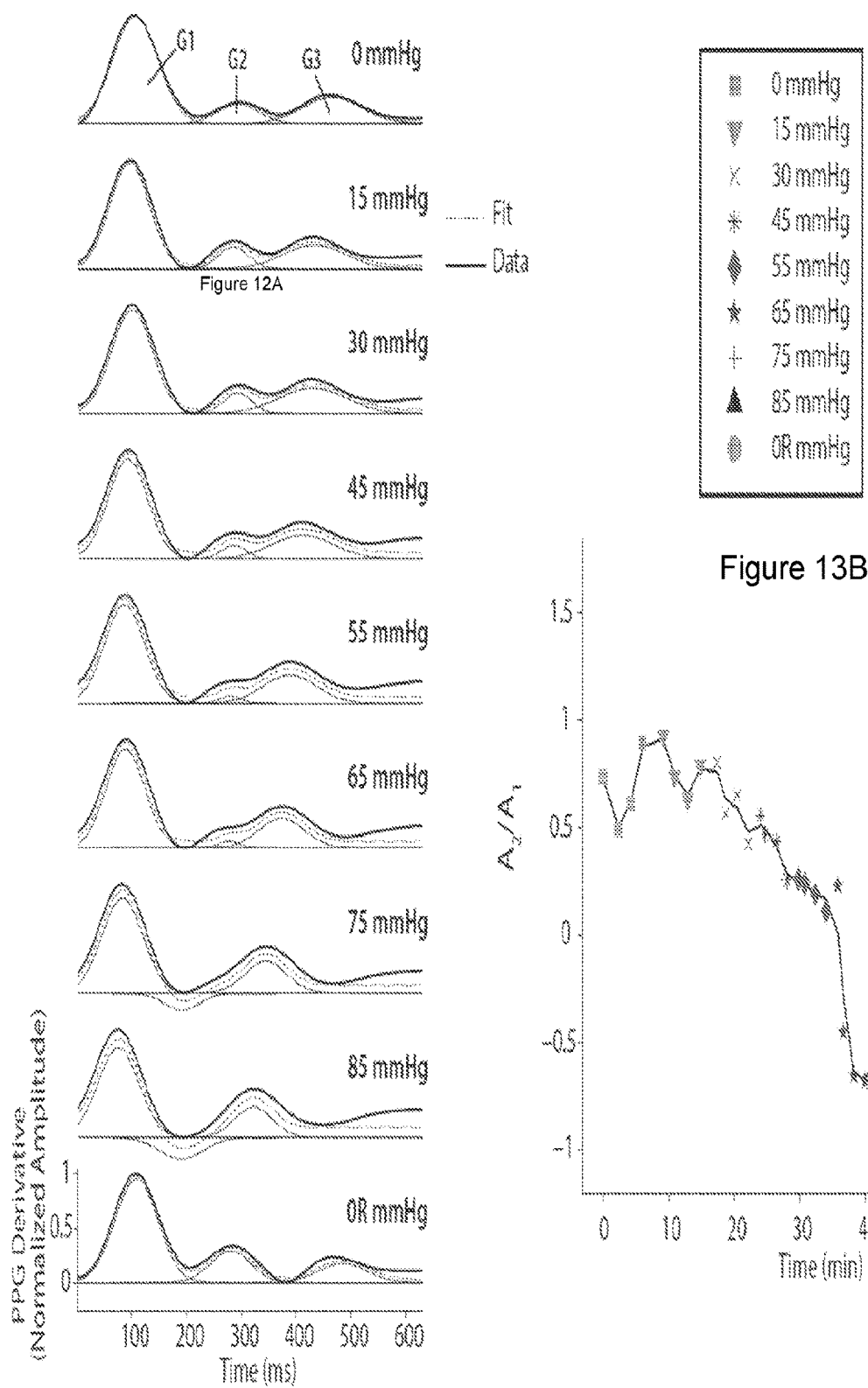
FIG. 13 is a plot of invention-derived pulse contour changes during lower body negative pressure.

Importantly, LVET is not the only cardiac function parameter that can be determined from the pulse contour. FIG. 13 shows an example of pulse contour decomposition analysis on data from the previously described lower body negative pressure (LBNP) protocol. Using roughly 1 minute blocks of data, an average PPG waveform is formed, and the derivative is computed and normalized to span from 0 to 1. A mixture of Gaussians model, of the form $y=\Sigma_{i=1}^{n} A_i e^{-(x-\mu_i)^2/(2\sigma_i^2)}+c$, is then fit to the derivative waveforms based on minimization of the sum of the squares of the errors. The free parameters are the amplitudes ($A_i$), centers ($\mu_i$) and width ($\sigma_i$) of the Gaussians, as well as the number of Gaussians used in the mixture (n) and an offset (c). In this example, the number of Gaussians is set to three. Examples of the waveforms and model fits are shown in FIG. 13A. Examination of the figure shows that as the level of LBNP increases and intravascular volume declines, the pulse contour undergoes several changes that are captured by the fit Gaussians (labeled G1, G2 and G3). The magnitude of the second wave is captured by parameter $A_2$, and reduces significantly with LBNP. As shown in FIG. 13B, the ratio between the amplitudes of the second and first waves, $A_2/A_1$, exhibits high sensitivity to the loss of blood volume and to the recovery of normal hemodynamic status when LBNP is released (OR mmHg). Thus, general pulse contour analysis can be used to assess cardiac function in a highly personalized manner.

Figure 14:
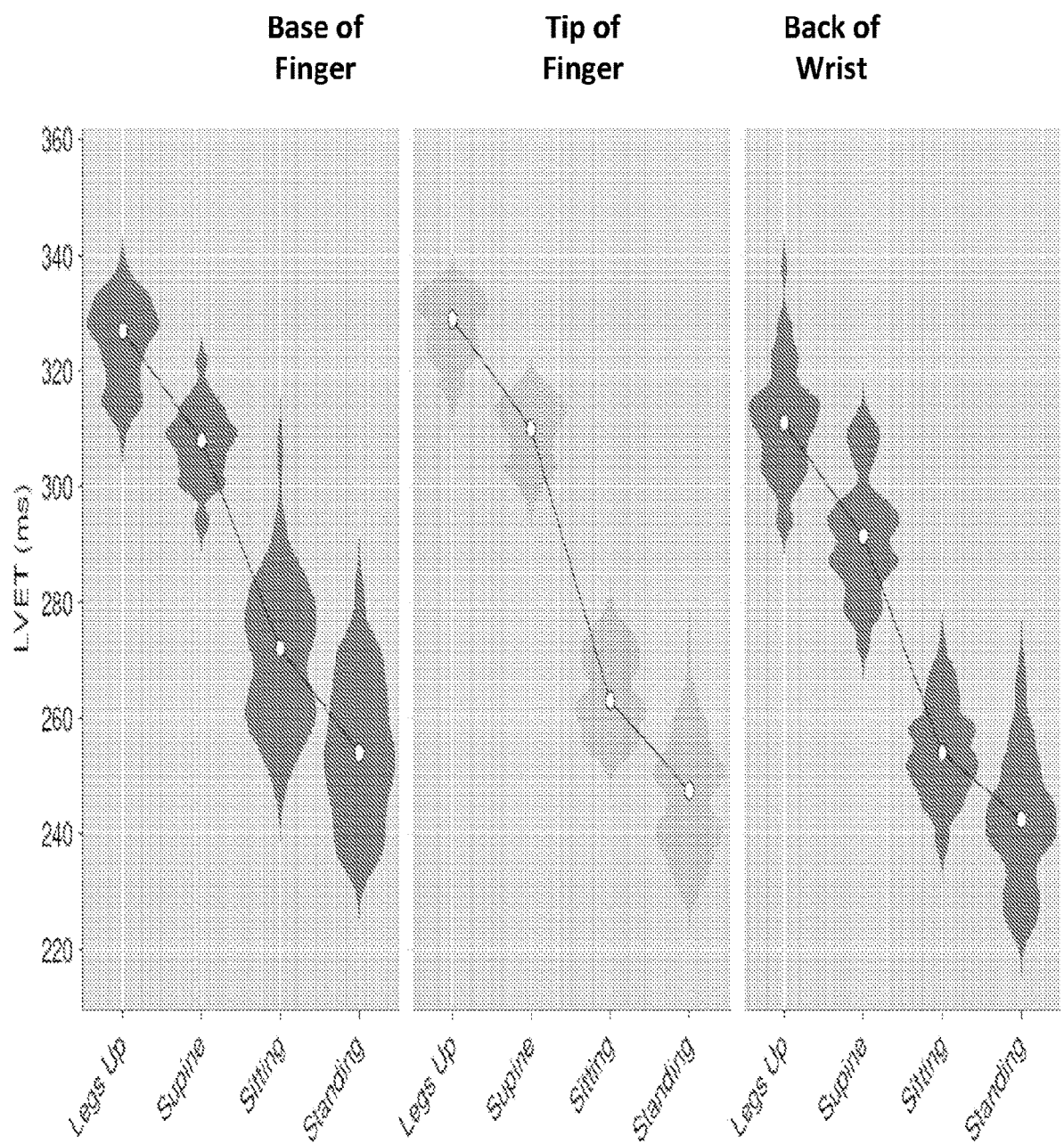
FIG. 14 is a plot of invention-derived LVET changes from multiple PPG locations.

Cardiac function parameters can be determined based on PPG signals acquired at the fingertip. However, changes in pulse contour as a function of venous return are also readily seen in PPG signals acquired from different locations on the body. FIG. 14 shows changes in LVET distribution as a function of body position for PPG signals acquired from the same individual at the base of the finger (ring location), tip of finger, and back of wrist (watch location). Substantial changes in LVET with changes in body position and hence venous return are observed for all three sites.

Heart Failure Monitoring System

The invention provides methods and systems for the noninvasive and observational assessment of heart failure, specifically the development of hemodynamic congestion. Embodiments of the invention contemplate two modes of operation, which modes can be used separately or in combination 2016-11-17. The first mode of operation comprises observing a patient during the activities of daily living and accessing cardiac function by examination of LVET (or other cardiac parameter) variation as a function of body position. The second mode of operation comprises tracking cardiac function parameters over time when the patient is in the same body position. These methods of accessing cardiac function, and specifically the occurrence of hemodynamic congestion, can be used independently or in combination in various embodiments of the invention.

Variation Monitoring for the Assessment of Hemodynamic Congestion

As noted in the referenced publications, increasing fluid volume or hemodynamic congestion decreases or blunts the normal cardiac response to body position changes. FIG. 15A shows the progression from normal fluid volume to fluid overload in a patient with heart failure. In the top-most graph (Observation Period #1), the patient's overall response mimics that of a normal patient in a normovolemic condition. The graph shows the stroke volume at the three main body positions: supine, sitting and standing. Note that in this example, stroke volume is used for the y-axis, but other cardiac function parameters can also be used. The bar on the right side of the plot denotes the span or variance in stroke volume observed in these three body positions.

As the same patient begins to retain fluid, end diastolic pressure increases, as shown by the right shift in the end diastolic pressure for the three body positions. For purposes of explanation, consider the patient in Observation Period #2 to be mildly fluid overloaded. The same three body positions are shown and will result in the same relative change in end diastolic pressure, however the cardiac response to the changes in body position will be different due to the location on the patient's Frank-Starling curve. Examination of the variance in stroke volume shows a marked decrease as evidenced by the shorter bar on the right. Observation Period #3 shows the same three body positions but with additional hemodynamic congestion. The additional fluid increases the end diastolic pressure further resulting in a further decrease in positional variance.

FIG. 15B summarizes change in stroke volume variance as measured during the three observation periods. The test leverages the fundamental repeatability of a within-patient test to create a personalized response surface that can be used for evaluation of possible congestive heart failure. This ability to conduct within-patient comparison testing over time and multiple measurement times per day creates a powerful diagnostic test for the assessment of heart failure decompensation.

Figure 15:
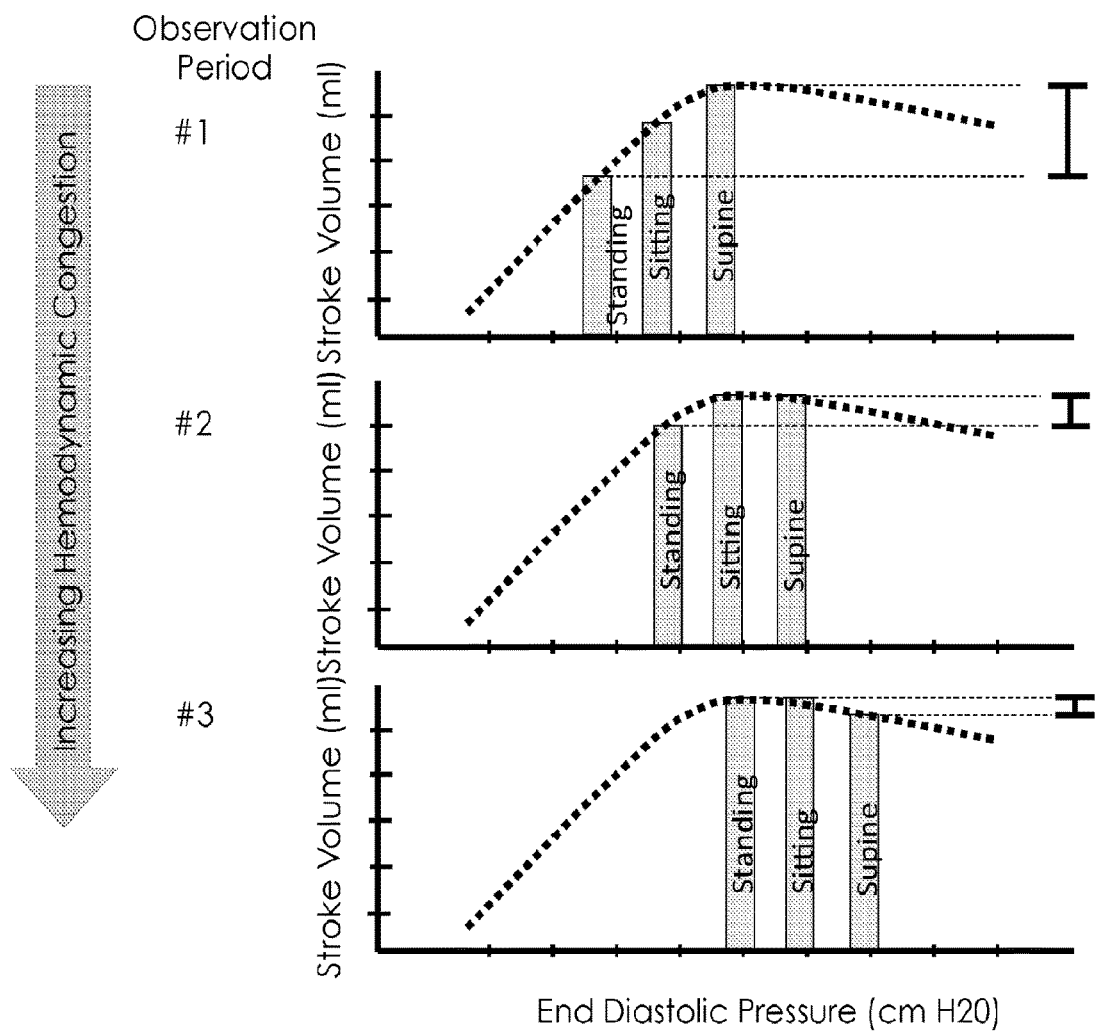
FIG. 15 is an illustration of increasing hemodynamic congestion.
Figure 15:
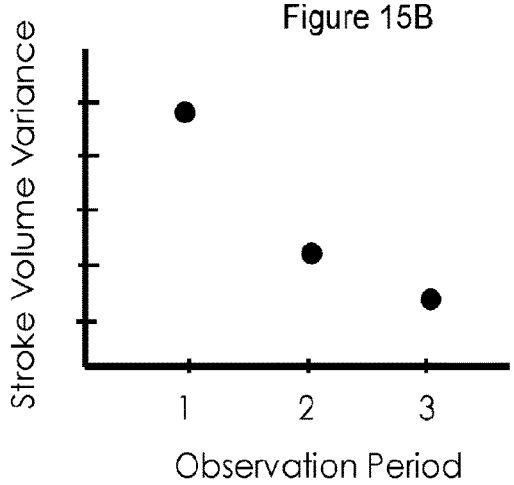
Figure 15:
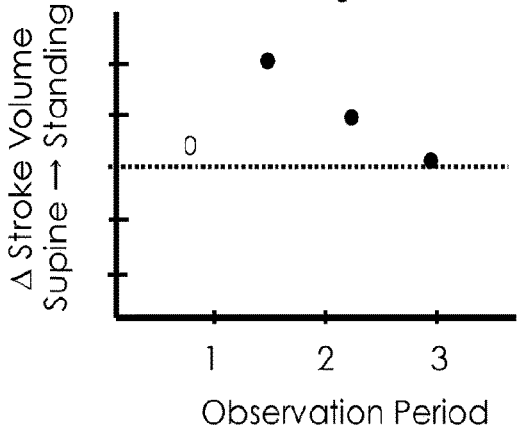

Evaluation of FIG. 15 also illustrates that the relative relationship between the cardiac function and body position changes with hemodynamic congestion. In Observation Period #1, the progression from supine to standing results in systematic decrease stroke volume, consistent with measured parameters shown in FIG. 8 and FIG. 9. In Observation Period #2, the transition between supine-sitting and standing does not create the same response. Specifically, the amount of cardiac function change between supine and sitting substantially diminished. In Observation Period #3, the change in stroke volume is opposite of Observation Period #1: there is an improvement in cardiac function as the patient transitions to body positions with less venous return. FIG. 15C summarizes the difference in stroke volume between supine and standing during the three observation periods. Importantly, the stroke volume difference during Observation Period #3 has become negative, a strong indication of hemodynamic congestion. Thus, the invention can make use of the relationship between cardiac parameters and different body position to provide valuable information that is highly diagnostic of the progression from a normovolemic state to hemodynamic congestion.

Illustrations of Variation Monitoring

The invention can perform an assessment of cardiac function variance in multiple ways. The following examples are illustrations; many other approaches exist and are contemplated in the present invention. In a first example, the body position assessment system can determine the body positions of supine, sitting and standing positions and identify periods of limited or no movement. Pulse signals can be obtained during these periods for a pre-determined time or until movement is detected. The measured PPG can be processed for the determination of cardiac function. In one example embodiment, the finger PPG signal is measured for 30 seconds and an LVET is determined for each pulse based upon the timing of the incisura. The resulting measures are averaged together and an average LVET for the body position is defined. The variation in average LVET measures across body positions is the computed and compared with historical values or a pre-determined threshold. Low variance is indicative of possible fluid overload.

In a second example, the variance assessment is compensated for possible differences in the time of day when positional data is acquired. Due to circadian rhythm changes that influence physiology, the data is processed with an awareness of when the positional data was obtained. For example, if standing data from the afternoon is used for the current variance assessment, the system will use previously acquired standing data from the afternoon. As used here, a similar time of the day is a general measure that can be defined, as examples, as morning, afternoon and evening. This time of day comparison process can improve diagnostic accuracy since most patients will awake at a fluid status lower than later in the day. To the extent possible, the system compares data from a similar time of the day with historical data from a similar time of the day so that the variance assessment is based upon position data acquired at similar times.

In a third example, the system focuses on the transitions between body positions and determines the direction and magnitude of changes in the cardiac function assessment parameter. For example, the transition from the supine position to the sitting position as the patient wakes up with subsequent progression to standing creates an opportunity for transition assessment that is repeatable on a daily basis.

In a fourth example, the system observes the cardiac response as the patient transitions from sitting to walking. For example, the system can define an observation as a transition from sitting to waking to include 5 steps at a given rate. The transition from sitting to walking requires the heart to compensate for increased physiological needs as well as decreased venous return. The response to these dual demands can be diagnostic for overall cardiac function. Each patient's response will be different but a personalized response can be created and used as a comparison for future assessments.

In a fifth example, continuous information from the body position assessment system is combined with cardiac assessment measures. The system acquires and processes data from all periods of the day and can include data acquired during movement. The resulting data can be used to create a personalized characterization of the patient's cardiac function and motion profile. Such data can be used to define a normal or typical response pattern for the patient and to evaluate novel data for abnormal behavior. Abnormal behavior for the purpose of heart failure management can include subtle changes associated with slowed or decreased movement, decreased heart rate variability, respiratory rate changes, and altered cardiac function response to typical movement. Although not used for heart failure management, Behavior Pattern Recognition (BPR) tools can be highly applicable in this example. BPR is a tactical tool for detection of suspicious terrorist and criminal behavior prior to an attack. It is designed as a preventive methodology, using unique behavior features of people involved in an extreme unlawful activity. Similar approaches can be used in the present invention to aggregate information over many days and to continuously update the methodology, creating a powerful tool for accessing small changes in cardiac function associated with the earliest manifestation of hemodynamic congestion.

Trend Monitoring for the Assessment of Hemodynamic Congestion

Figure 16:
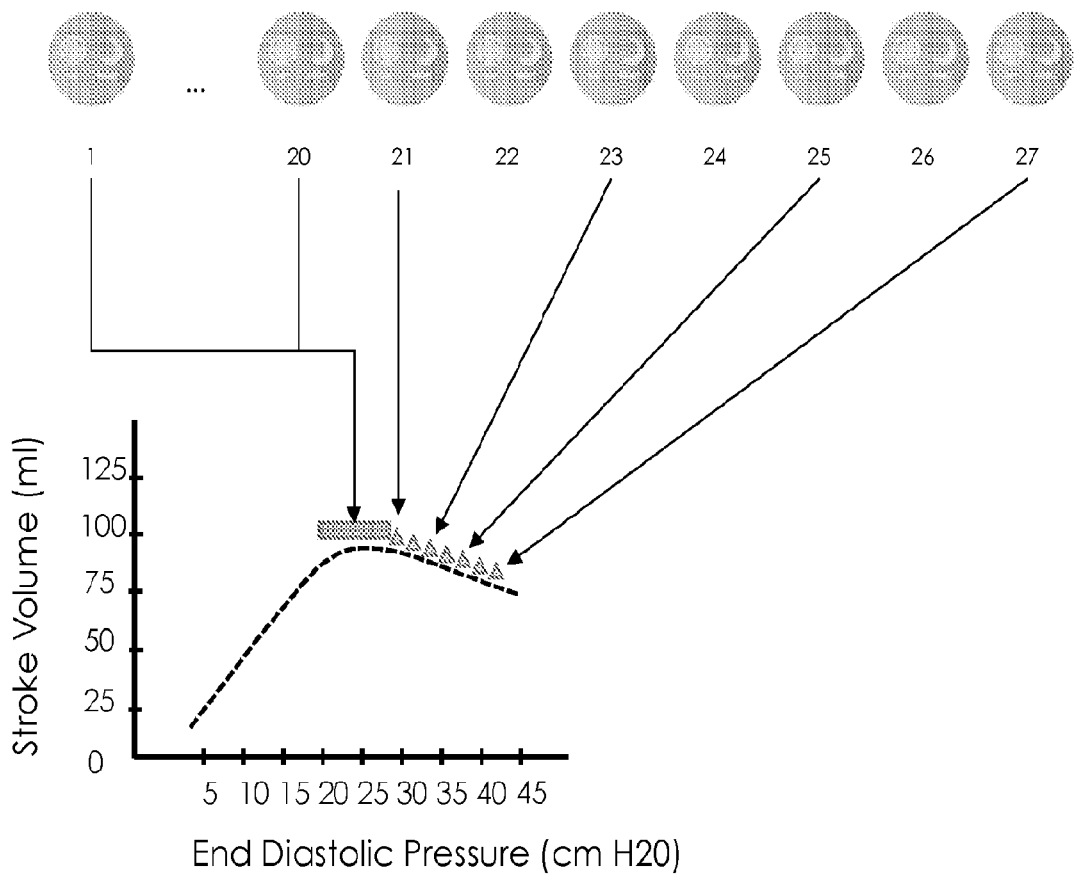
FIG. 16 is an illustration of multi-day hemodynamic monitoring.
Figure 16:
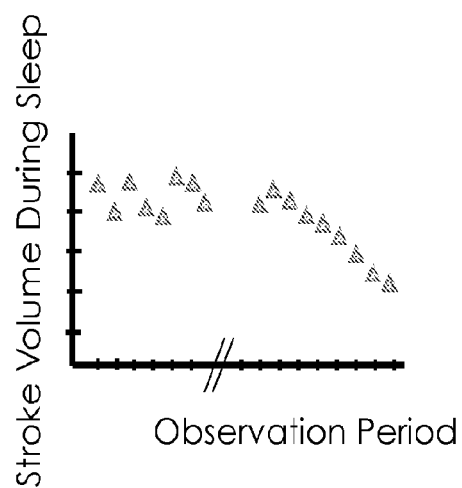

A second mode for determining heart failure decompensation assesses cardiac function over time when the patient is in the same body position. For example, the system can assess the patient's cardiac function while sleeping, even during the same stage of sleep every night. This type of sleep stage assessment creates a repeatable cardiac assessment than can be evaluated on a day-to-day basis. As an example, the system can acquire and process data obtained during the same sleep stage at least once during the night. The average or minimum LVET can then be compared against prior LVET measurements for the determination of any temporal trend. FIG. 16 is an example of such a monitoring process. As illustrated in the FIG. 16, the patient experienced no systematic changes over days 1 to 20, but begins to experience decreased cardiac function as depicted by decreased stroke volume on Day 21. This trend of decreased stroke volume continues for the 7 days, clearly indicating fluid overload and hemodynamic congestion. The system can provide an early indicator of decompensation such that interventions can be administered in the ambulatory setting and an admission to the hospital avoided.

Attached Body Position Assessment Systems

Body position assessment by use of attached sensors is an area of interest in video game entertainment. Other uses include activity tracking in the elderly, as well as motion tracking in sports. For example, Najafi et al. demonstrated a new method of physical activity monitoring that differentiated multiple body postures (sitting, standing, and lying) and periods of walking in elderly persons using only one kinematic sensor attached to the chest. Najafi, B., Aminian, K., Paraschiv-Ionescu, A., Loew, F., C. J., & Robert, P. (2003). Ambulatory system for human motion analysis using a kinematic sensor: Monitoring of daily physical activity in the elderly. IEEE Transactions on Biomedical Engineering, 50(6), 711-723. http://doi.org/10.1109/TBME.2003.812189. Najafi et al. have also published on a gyroscope-only system. Najafi, B., Aminian, K., Loew, F., Blanc, Y., Robert, P. a, & Member, S. (2002). Measurement of Stand-Sit and Sit-Stand Transitions Using a Miniature Gyroscope and Its Application in Fall Risk Evaluation in the Elderly. IEEE Transactions on Biomedical Engineering, 49(8), 843-851. http://doi.org/.10.1109/TBME.2002.800763. Other examples of position monitoring have been used with ambulatory EKG monitoring. Jason et al. demonstrated the ability to determine a patient's position (lying down, sitting, standing, or changing from one position to another) during Holter monitoring for the evaluation of common symptoms such as dizziness, palpitations, and syncope. Akhtar, S., Matei, V., London, M. J., & Barash, P. G. (2011). Electrocardiographic Monitoring. Kaplan's Cardiac Anesthesia: The Echo Era, 60208, 452-465. The system referenced above uses sensors attached to the patient's chest, not on the hand, wrist or finger. For convenience and consistency with normal daily living the invention can achieve similar performance using a wrist or ring based sensor for the determination of body position.

The system can use motion sensors in a ring or watch to determine gross measurements of physical activity and classify activity types. The system can use activity classification to facilitate determination of body position. For example, if the activity of rising from a chair is detected, the body position can be determined as standing. Activity recognition and the surrounding sequence of activities can be highly deterministic of the body position, particularly with the use of state-space models. Because motion patterns are somewhat specific to each individual, the system can be trained during an initial training period during which the patient indicates when they have moved into a supine, sitting or standing position.

Additional information on body position can be acquired by using the angle of inclination and rotation of a sensor, which are easily measured with a 3-axis accelerometer. Rotational information can indicate if the hand is in a position consistent with standing, sitting or lying down. For example, sleeping can be accessed identifying an activity consistent with going to bed, followed by prolonged periods of minimal or no activity, and an orientation of the sensor consistent with the hand resting on the bed.

The body position system is used to ensure that various body positions have been achieved. If no variance in body position is achieved over the course of the day, then the cardiac function variance will be diminished and the potential for a false positive result increased. In the situation where the patient has failed to change body position over a designated period, the system can prompt the patient to change body positions. The system can provide this type of quality control associated with the observational test to help ensure diagnostic accuracy.

Unattached Body Position Assessment Systems.

The activity of entering or exiting a bed, or exiting to and from a table create observational opportunities that can be captured and quantified by imaging systems. The actions of the patient can be determined using an imaging system. An imaging system can be located on the bed stand or the kitchen and used to capture video information. The system can process the resulting data using vision-based activity recognition and subsequent position determination. Vision-based activity recognition is the process of labeling video information containing human motion with action or activity labels.

Such a system can be implemented using a variety of vision capture technologies to include both video and cameras. As an example, a motion-based video camera with human detection can be used to capture the patient's movement. The system can identify the patient using face recognition technology or by having a sensor on or with the patient emit a signal. The signal can take many forms including electromagnetic signals, RFID tags or an optical signal. A blinking infrared LED can leverages the infrared video recording that is common to many motion detection video cameras. The video system can track the subject or use a fisheye (ultra wide-angle) lens to completely capture the scene.

The system can also use structured light or a 3D camera system such as the Microsoft Kinect, Orbbec Astra, Intel Realsense, or Stereolabs Zeb stereo camera, to create a 3-dimensional image. Multiple systems can do skeletal tracking for the creation of a skeleton stick figure that captures the movements of the individual. Han et al. have recently written a review article that presents a comprehensive survey of existing space-time representations of people based on 3D skeletal data, and provides an informative categorization and analysis of these methods from the perspectives of information modality, representation encoding, structure and transition, and feature engineering. Han, Fei, et al. "." arXiv preprint arXiv:1601.01006 (2016).

In addition to the use of vision-based activity recognition, the system can use face detection for determining the general position of the patient. Face detection is a computer technology being used in a variety of applications that identifies human faces in digital images. In 2001, Paul Viola and Michael Jones invented a new framework for detecting arbitrary objects and refined it for face detection. The algorithm is now known as the Viola-Jones framework. The Viola-Jones method has a very high accuracy rate and does not require significant processing power. As used in the invention, face detection can be used to locate the face in the image and infer body position as supine, sitting or standing.

Sleep Cycle Assessment.

Human physiology varies based upon the sleep stage of the patient. Known physiological changes include changes in blood pressure, heart rate, respiratory rate, heart rate variability, temperature, motion, and respiratory variability. Determination of sleep stage has been an active area of physiological study. Polysomnography is considered the gold standard to assess sleep accurately, but it can be expensive, time consuming and uncomfortable, specifically in long-term sleep studies. Actigraphy provides a precise measurement of the motion of the part of the body to which a device is attached. The technology can assess sleep/wake patterns and is both cheap and user friendly, but depending on the application lacks detail (such as the REM-NREM distinction). The system can address this limitation by adding a PPG signal. During non-REM sleep, heart rate and respiratory rate decrease whereas during REM sleep breathing and heart rate become more irregular. The system thus can provide a watch or other system containing a motion sensor as well as a PPG signal and can enable determination of the sleep phase.

Communication System.

Remote monitoring is a mechanism that enables communication of cardiac function information for the patient to a remote assessment site, the physician or clinic office. The system enables communication between the assessment system and the doctor's office, without having to a direct face-to-face interaction.

System Elements and Embodiments

The heart failure system can be described in terms of three general elements: (1) pulse detection system, (2) body position sensing system, and (3) a communication system. Embodiments can take many forms, including a single system that contains all three systems, or three independent systems that interact with each other.

Embodiment Number 1

Figure 17:
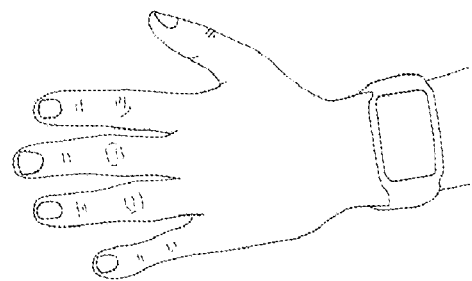
FIG. 17 is an example of a single unit heart failure monitoring system.

A single system example embodiment is composed all three system in a single housing. FIG. 17 is an example of a watch that contains a PPG measurement system, motion sensors (multi-access accelerometers and gyroscopic sensors), and a Wi-fi or internet-on-a-chip subsystem. In practice the patient wears the watch and the watch continuously or intermittently monitors the patient. Due to power consumption issues, the system can do smart sampling based upon motion and activity recognition. For example, the watch can start the daily assessment by identifying a sleeping period with no or limited motion followed by an assessment that the patient is in defined sleep stage. The system can then acquire PPG data for a period and perform appropriate quality control on the data to ensure effective supine body position data. The system can then move to a low energy state until it detects movement into the sitting or standing position, and then can acquire additional PPG data. The system can repeat the above body position recognition process and acquire data over the course of the day. The system can transmit data for subsequent medical evaluation throughout the day when the system is connected to a Wi-fi connection. Additionally, the data can be uploaded at night. The sensor system can provide haptic, auditory and/or visual feedback to the patient to communicate the acquisition of data and whether data quality was determined to be inadequate. Possible causes of inadequate data include poor placement of the watch, loose watch band, excessive motion, limited movement by the patient, or other movement oddities. The system can provide recommendations for resolution of the problem.

Embodiment Number 2

Figure 18:
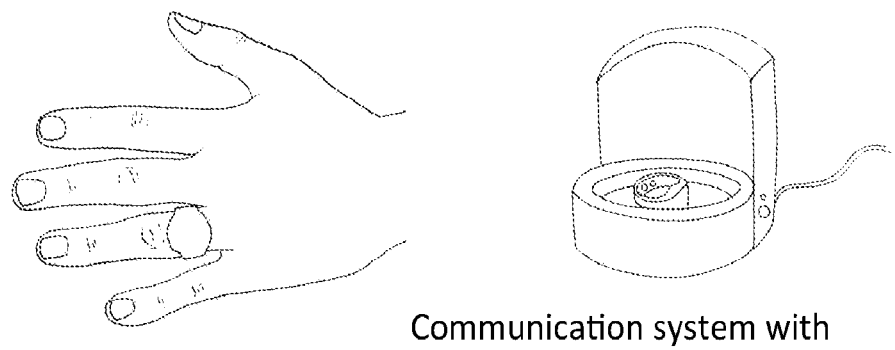
FIG. 18 is an example of a two-unit heart failure monitoring system.

The example embodiment of a heart failure monitoring system can comprise two components: a ring-based PPG and a communication system. The ring can include a PPG measurement system, an inertial measurement unit, and a Bluetooth wireless communication system. The ring system communicates with a separate data transmission station. The data transmission station can communicate via the internet, via cellular communication or by modem. FIG. 18 is an illustration of such a system.

Embodiment Number 3

Figure 19:
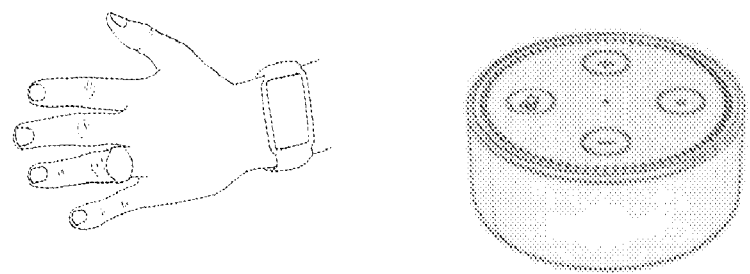
FIG. 19 is an example of a three-unit heart failure monitoring system.

The example embodiment of a heart failure monitoring system can comprise three units: a ring, a watch and a communication system. In one example, the ring and watch work in conjunction to acquire the best possible PPG signal. If the wrist PPG signal is not adequate, then the ring is activated to procure a PPG signal. The benefit of such a system is the ability to locate a larger battery on the wrist as well as additional sensors in the wrist based system. FIG. 19 is an illustration of such a system comprising the ring sensor, watch electronics and motion sensors and a communication system.

Embodiment Number 4

Figure 20:
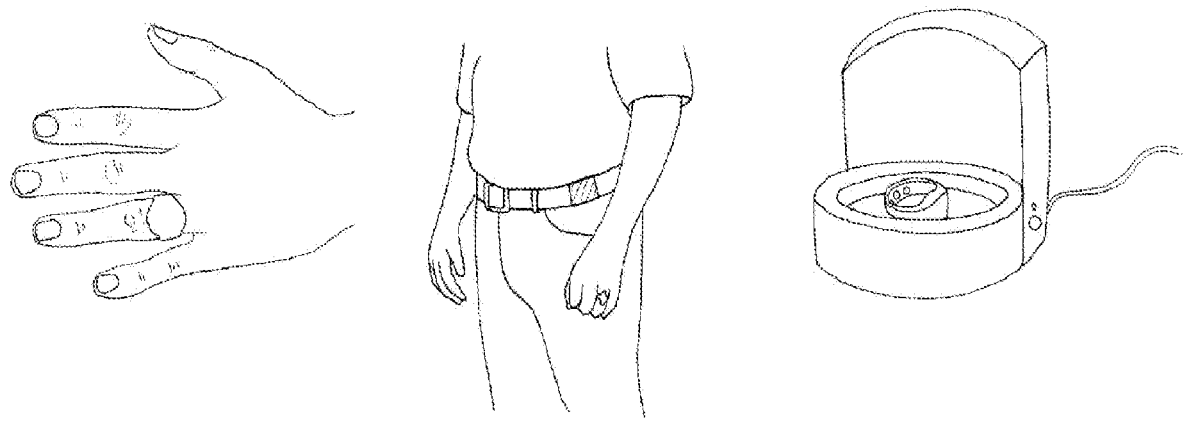
FIG. 20 is an example of a heart failure monitoring system with a waist belt motion sensor.

The example embodiment of a heart failure monitoring system can comprise three units: a ring-based PPG, one or more kinematic sensors used to determine body position, and a communication system. The kinematic sensors can be placed at multiple points on the body such as the torso, feet, or hips to determine body position in addition to body activity. For example, if the torso sensor is oriented vertically, it is highly likely that the subject is sitting or standing. Sensors can be integrated into wearable items such as necklaces, shoes, or belts, such that they would not interfere with daily activities. The kinematic and PPG sensors can communicate with the data transmission system using a protocol such as Bluetooth. FIG. 20 is an illustration of such a system with a ring sensor, waist mounted motion sensor and communication system.

Embodiment Number 5

Figure 21:
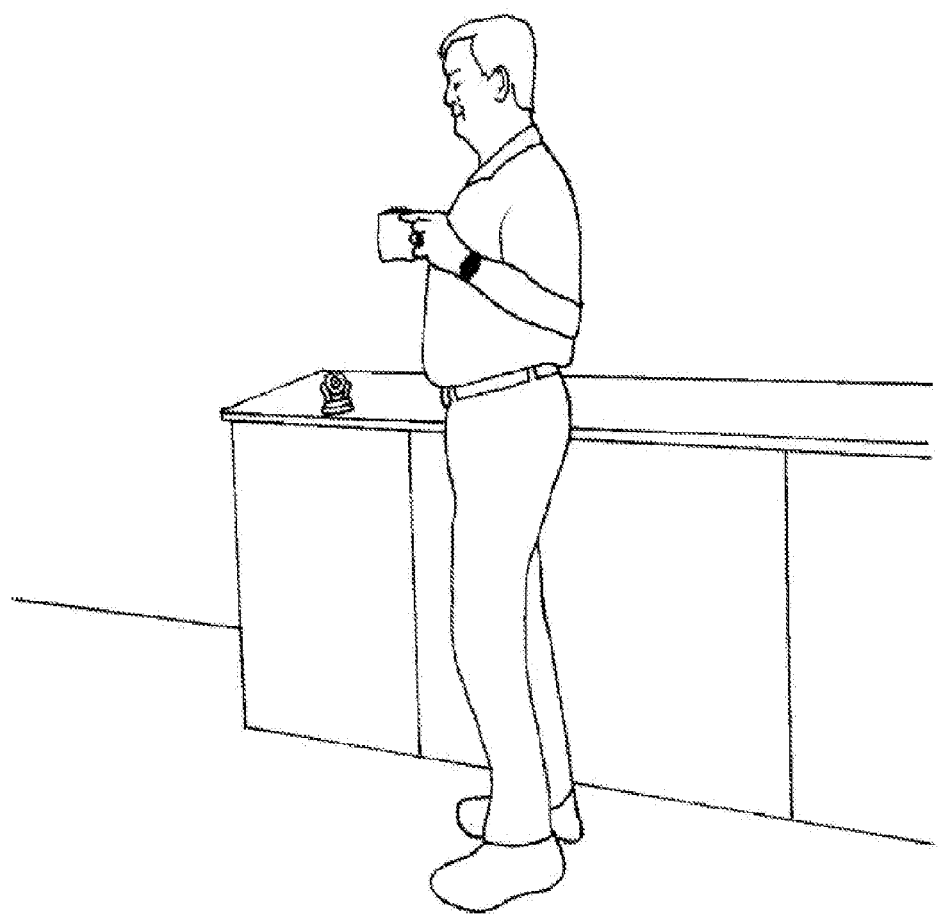
FIG. 21 is an illustration of a camera based body position sensor.

The example embodiment of a heart failure monitoring system can comprise a pulse sensor attached to the subject and a combined communication/body position measurement system. The combined communication and position measurement system can contain a video camera for capturing images of the patient, for example in the kitchen. The camera enables the determination of body position. The pulse sensor communicates with the communication system and the images and data can be uploaded for remote processing, if desired. In use, the pulse sensor system acquires data in the supine position at night while other data is be captured while in the kitchen. The communication system can also contain a speaker and additional hardware so that video communication with the physician can occur. FIG. 21 is an illustration of the camera system and the system in use.

The illustrations and embodiments have been described herein in the context of hemodynamic monitoring in the patient with heart failure. The system also is applicable to the monitoring of hypovolemia. The system can provide monitoring of a post-surgical patient for the assessment of bleeding or inadequate fluid consumption. The assessment of volume status in the elderly can be difficult because these patients often present as confused. The diagnostic work-up can include severe conditions such as stroke or more simply treated conditions such as hypovolemia. Embodiments of the present invention can be used to monitor older adults for the development of hypovolemia.

The present invention has been described in connection with various example embodiments. It will be understood that the above description is merely illustrative of the applications of the principles of the present invention, the scope of which is to be determined by the claims viewed in light of the specification. Other variants and modifications of the invention will be apparent to those skilled in the art.

The invention claimed is:

1. A method of assessing the volume status of an individual, comprising:
   (a) measuring a first pulse contour of the individual from a first cardiac cycle with a noninvasive wearable sensor;
   (b) measuring a second pulse contour with the noninvasive wearable sensor, where the second pulse contour is measured from a second cardiac cycle, different from the first cardiac cycle;
   (c) determining a first metric of left ventricular output from the first pulse contour based on temporal relationships between features within the first pulse contour;
   (d) determining a second metric of left ventricular output from the second pulse contour based on temporal relationships between features within the second pulse contour;
   (e) determining a measure of variation between the first and second metrics;
   (f) assessing the volume status of the individual from the measure of variation.

2. A method as in claim 1, further comprising detecting a change in the body position of the individual during an activity of daily living after the measurement in (a); and wherein measuring a second pulse contour of the individual comprises measuring a second pulse contour with the noninvasive wearable sensor after the change in body position has been detected.

3. A method as in claim 2, wherein detecting a change in the body position of the individual during an activity of daily living comprises detecting a first body position of the individual during the measurement in (a), then detecting a change in the body position to a position other than the first body position, then detecting a return of the body position to the first body position.

4. A method as in claim 3, wherein the first and second pulse contours are measured while the individual is in the same sleep stage.

5. A method as in claim 2, wherein the body position is determined by a sensor not attached to the individual.

6. A method as in claim 5, wherein the body position is determined by an optical sensing system.

7. A method as in claim 1, wherein the second pulse contour is measured at least 3 hours after the first pulse contour is measured.

8. A method as in claim 1, wherein assessing the volume status comprises determining a degree of hemodynamic congestion.

9. A method as in claim 1, wherein the first and second pulse contours are measured while the individual is in the same sleep stage.

10. A method as in claim 1, wherein assessing the volume status comprises comparing the measure of variation with a measure of variation previously determined for the individual.

11. A method as in claim 1, wherein the wearable sensor is attached to a finger of the individual.

12. A method as in claim 1, wherein the wearable sensor comprises a PPG sensor.

13. A method as in claim 1, wherein the metric of left ventricular output is the duration of ventricular ejection.

14. A method as in claim 1, wherein assessing the volume status comprises determining a fluid status of the individual.

15. An apparatus for assessing volume status of an individual, comprising:
   (a) a noninvasive sensor configured to be worn by an individual and to measure a pulse contour;
   (b) a measurement control system configured to use the noninvasive sensor to measure a first pulse contour and a second pulse contour, where the first pulse contour and the second pulse contour are from different cardiac cycles;
   (c) an analysis system configured to determine a first metric of left ventricular output from the first pulse contour based on temporal relationships between features within the first pulse contour, and to determine a second metric of left ventricular output from the second pulse contour based on temporal relationships between features within the second pulse contour, and to determine a measure of variation between the first metric and the second metric, and to assess the volume status from the measure of variation.

16. An apparatus as in claim 15, wherein the noninvasive sensor is configured to mount with a distal aspect of an upper limb of the individual.

17. An apparatus as in claim 16, wherein the noninvasive sensor is configured to mount with a finger of the individual.

18. An apparatus as in claim 16, wherein the noninvasive sensor comprises a PPG sensor.

19. An apparatus as in claim 16, wherein the noninvasive sensor is configured to avoid interference with activities of daily living.

20. An apparatus as in claim 15, further comprising a body position subsystem configured to determine a body position of an individual.

21. An apparatus as in claim 15, wherein the measurement control system is configured to measure the second pulse contour responsive to a signal from the body position subsystem indicating that the body position of the individual has changed after the measurement of the first pulse contour.

22. An apparatus as in claim 15, wherein the measurement control system is configured to measure the second pulse contour responsive to a signal from the body position subsystem indicating that the body position of the individual has returned to the body position of the individual during measurement of the first pulse contour.

* * * * *